United States Patent
Honarpour et al.

(10) Patent No.: US 11,576,910 B2
(45) Date of Patent: Feb. 14, 2023

(54) METHODS OF TREATING HEART FAILURE WITH CARDIAC SARCOMERE ACTIVATORS

(71) Applicants: AMGEN INC., Thousand Oaks, CA (US); CYTOKINETICS, INC., South San Francisco, CA (US)

(72) Inventors: Narimon Honarpour, Thousand Oaks, CA (US); Fady Malik, South San Francisco, CA (US)

(73) Assignees: AMGEN INC., Thousand Oaks, CA (US); CYTOKINETICS, INC., South San Francisco, CA (US)

( * ) Notice: Subject to any disclaimer, the term of this patent is extended or adjusted under 35 U.S.C. 154(b) by 106 days.

(21) Appl. No.: 16/625,958

(22) PCT Filed: Jun. 29, 2018

(86) PCT No.: PCT/US2018/040181
§ 371 (c)(1),
(2) Date: Dec. 23, 2019

(87) PCT Pub. No.: WO2019/006235
PCT Pub. Date: Jan. 3, 2019

(65) Prior Publication Data
US 2020/0155547 A1 May 21, 2020

Related U.S. Application Data

(60) Provisional application No. 62/527,983, filed on Jun. 30, 2017.

(51) Int. Cl.
*A61K 31/496* (2006.01)
*A61K 9/00* (2006.01)
*A61P 9/04* (2006.01)

(52) U.S. Cl.
CPC .......... *A61K 31/496* (2013.01); *A61K 9/0053* (2013.01); *A61P 9/04* (2018.01)

(58) Field of Classification Search
CPC ........ A61K 31/496; A61K 9/0053; A61P 9/04
See application file for complete search history.

(56) References Cited

U.S. PATENT DOCUMENTS

| | | | |
|---|---|---|---|
| 4,450,150 A | 5/1984 | Sidman | |
| 7,507,735 B2 | 3/2009 | Morgan et al. | |
| 8,101,617 B2 | 1/2012 | Morgan et al. | |
| 8,110,595 B2 | 2/2012 | Morgan et al. | |
| 8,445,495 B2 | 5/2013 | Morgan et al. | |
| 8,513,257 B2 | 8/2013 | Morgan et al. | |
| 8,871,768 B2 | 10/2014 | Morgan et al. | |
| 8,871,769 B2 | 10/2014 | Morgan et al. | |
| 9,150,564 B2 | 10/2015 | Morgan et al. | |
| 9,643,925 B2 | 5/2017 | Morgan et al. | |
| 9,895,308 B2 | 2/2018 | Caldwell | |
| 9,951,015 B2 | 4/2018 | Bi et al. | |
| 9,988,354 B2 | 6/2018 | Cui et al. | |
| 10,035,770 B2 | 7/2018 | Morgan et al. | |
| 10,385,023 B2 | 8/2019 | Morgan et al. | |
| 10,421,726 B2 | 9/2019 | Bi et al. | |
| 10,543,215 B2 | 1/2020 | Scott et al. | |
| 10,975,034 B2 | 4/2021 | Morgan et al. | |
| 2007/0161617 A1 | 7/2007 | Morgan et al. | |
| 2009/0036447 A1 | 2/2009 | Morgan et al. | |
| 2009/0099198 A1 | 4/2009 | Morgan et al. | |
| 2010/0029680 A1 | 2/2010 | Morgan et al. | |
| 2012/0172372 A1 | 7/2012 | Morgan et al. | |
| 2013/0324549 A1 | 12/2013 | Morgan et al. | |
| 2014/0038983 A1 | 2/2014 | Morgan et al. | |
| 2014/0309235 A1 | 10/2014 | Bi et al. | |
| 2015/0005296 A1 | 1/2015 | Morgan et al. | |
| 2016/0015628 A1* | 1/2016 | Caldwell .............. | A61K 9/0004 424/465 |
| 2016/0016906 A1 | 1/2016 | Cui et al. | |
| 2016/0115133 A1 | 4/2016 | Morgan et al. | |
| 2017/0267638 A1 | 9/2017 | Morgan et al. | |
| 2018/0140611 A1 | 5/2018 | Scott et al. | |
| 2018/0273479 A1 | 9/2018 | Bi et al. | |
| 2018/0305316 A1 | 10/2018 | Morgan et al. | |
| 2018/0312469 A1 | 11/2018 | Cui et al. | |
| 2019/0352267 A1 | 11/2019 | Morgan et al. | |
| 2020/0079736 A1 | 3/2020 | Cui et al. | |
| 2020/0108076 A1 | 4/2020 | Scott et al. | |

(Continued)

FOREIGN PATENT DOCUMENTS

WO 1999/40942 A1 8/1999
WO 2000/32218 A1 6/2000

(Continued)

OTHER PUBLICATIONS

NCT01786512—COSMIC-HF—Chronic Oral Study of Myosin Activation to Increase Contractility in Heart Failure (May 5, 2016 copy attached; downloaded from the web Nov. 19, 2021 (Year: 2016).*

Teerlink et al. Acute Treatment With Omecamtiv Mecarbil to Increase Contractility in Acute Heart Failure The ATOMIC-AHF Study, JACC vol. 67, No. 12, 2016, Mar. 29, 2016: 1444-55 (Year: 2016).*

Fady I. Malik, Bradley P. Morgan, Cardiac myosin activation part 1: From concept to clinic, Journal of Molecular and Cellular Cardiology 51 (2011) 454-46 (Year: 2011).*

(Continued)

*Primary Examiner* — Kortney L. Klinkel
*Assistant Examiner* — Jason Deck
(74) *Attorney, Agent, or Firm* — Morrison & Foerster LLP

(57) ABSTRACT

Provided herein are methods of treating a subject with heart failure, comprising administering to the subject an initial dose of a cardiac sarcomere activator (CSA) for an initial time period, and subsequently administering to the subject a dose of the CSA based on the subject's plasma concentration of the CSA at the end of the initial time period.

39 Claims, 4 Drawing Sheets

(56) References Cited

U.S. PATENT DOCUMENTS

| | | |
|---|---|---|
| 2020/0277261 A1 | 9/2020 | Bi et al. |
| 2020/0308143 A1 | 10/2020 | Caille et al. |
| 2020/0331859 A1 | 10/2020 | Cui et al. |
| 2020/0399221 A1 | 12/2020 | Cui et al. |
| 2021/0198203 A1 | 7/2021 | Morgan et al. |
| 2021/0221772 A1 | 7/2021 | Man et al. |
| 2021/0292271 A1 | 9/2021 | Brasola et al. |

FOREIGN PATENT DOCUMENTS

| | | |
|---|---|---|
| WO | 2004/033036 A2 | 4/2004 |
| WO | 2007/133747 A2 | 11/2007 |
| WO | 2007/141411 A1 | 12/2007 |
| WO | 2008/130158 A1 | 10/2008 |
| WO | 2014/152236 A1 | 9/2014 |
| WO | 2016/210240 A1 | 12/2016 |

OTHER PUBLICATIONS

U.S. Appl. No. 15/898,303, filed Feb. 16, 2018, by William Brett Caldwell et al. (The U.S. Patent Application is not submitted herewith pursuant to the waiver of 37 C.F.R. § 1.98(a)(2)(iii) issued by the Office on Sep. 21, 2004.).

U.S. Appl. No. 17/176,003, filed Feb. 15, 2021, by Sheng Cui et al. (The U.S. Patent Application is not submitted herewith pursuant to the waiver of 37 C.F.R. § 1.98(a)(2)(iii) issued by the Office on Sep. 21, 2004.).

U.S. Appl. No. 17/258,385, filed Jan. 6, 2021, by Elena Brasola et al. (The U.S. Patent Application is not submitted herewith pursuant to the waiver of 37 C.F.R. § 1,98(a)(2)(iii) issued by the Office on Sep. 21, 2004.).

U.S. Appl. No. 17/263,224, filed Jan. 26, 2021, by Henry Morrison et al. (The U.S. Patent Application is not submitted herewith pursuant to the waiver of 37 C.F.R. § 1,98(a)(2)(iii) issued by the Office on Sep. 21, 2004.).

U.S. Appl. No. 17/309,727, filed Jun. 16, 2021, by Serena Bisagni et al. (The U.S. Patent Application is not submitted herewith pursuant to the waiver of 37 C.F.R. § 1,98(a)(2)(iii) issued by the Office on Sep. 21, 2004.).

U.S. Appl. No. 17/324,867, filed May 19, 2021, by Sebastien Caille et al. (The U.S. Patent Application is not submitted herewith pursuant to the waiver of 37 C.F.R. § 1,98(a)(2)(iii) issued by the Office on Sep. 21, 2004.).

Solomon et al., Effect of candesartan on cause-specific mortality in heart failure patients the candesartan in heart failure assessment of reduction in mortality and morbidity (CHARM) program, Circulation, 110:2180-2183 (2004).

Solomon et al., Effect of cardiac resynchronization therapy on reverse remodeling and relation to outcome: multicenter automatic defibrillator implantation trial: cardiac resynchronization therapy, Circulation, 122:985-992 (2010).

Steijns et al., Evaluation of fluorescence polarization assays for measuring valproic acid, phenytoin, carbamazepine and phenobarbital in serum, Ther. Drug. Monit., 24:432-435 (2002).

Tacon et al., Dobutamine for patients with severe heart failure: a systematic review and meta-analysis of randomised controlled trials, Intensive Care Med., 38(3):359-367 (2012).

Teerlink et al., Acute treatment with omecamtiv mecarbil to increase contractility in acute heart failure: the Atomic AHF study, J. Am Coll. Cardiol., 67:1444-1455 (2016).

Teerlink et al., Chronic Oral Study of Myosin Activation to Increase Contractility in Heart Failure (COSMIC-HF): a phase 2, pharmacokinetic, randomised, placebo-controlled trial, The Lancet., 388:2895-2903 (2016).

Teerlink et al., Dose-dependent augmentation of cardiac systolic function with the selective cardiac myosin activator, omecamtiv mecarbil: a first-in-man study, Lancet, 378:667-675 (2011).

Thygesen et al., Third universal definition of myocardial infarction, J. Am. Coll. Cardiol., 60:1581-1598 (2012).

Toissel, ASHP handbook on injectable drugs, 4th ed., 622-630 (1986).

Vu et al., Population pharmacokineticpharmacodynamic modeling of omecamtiv mecarbil, a cardiac myosin activator, in healthy volunteers and patients with stable heart failure, J Clin. Pharmacol., 55:1236-1247 (2015).

Waldenstrom et al., Role of exosomes in myocardial remodeling, Circ. Res., 114:315-324 (2014).

Wang et al., Measurement of plasma concentration and bioavailability of nolatrexed dihydrochloride in mice, Nan Fan Yi Ke Da Xue Xue Bao., 28(11):1993-1995 (2008).

Weissler et al., Systolic time intervals in heart failure in man, Circulation, 37:149-159 (1968).

Yancy et al., ACC/AHA/HFSA Focused update on new pharmacological therapy for heart failure: An update of the 2013 ACCF/AHA guideline for the management of heart failure, Circulation, Epub ahead of print, PMID 27208050, doi: 10.1161/CIR.0000000000000435 (2016).

Yancy et al., ACCF/AHA guideline for the management of heart failure: A report on the american college of cardiology foundation/american heart association task force on practice guidelines, Circulation, 128:e240-e327 (2013).

Adjei et al., Pulmonary delivery of peptide drugs: Effect of particle size on bioavailability of leuprolide acetate in healthy male Volunteers, Pharmaceutical Research, 7(6):565-569 (1990).

Ambrosy et al., The global health and economic burden of hospitalizations for heart failure, J. Am. Coll. Cardiol., 63(12):1123-1133 (2014).

Apple, A., new season for cardiac troponin assays: it's time to keep a scorecard, Clin. Chem., 55:1303-1306 (2009).

Banker et al., Pharmaceutics and pharmacy practice, J. B. Lippincott Company, Philadelphia, PA, 238-250 (1982).

Bhatia et al., Outcome of heart failure with preserved ejection fraction in a population-based study, N. Engl. J. Med., 355(3):260-269 (2006).

Biering-Sorensen et al., Systolic ejection time is an independent predictor of incident heart failure in a community based cohort free of heart failure, J. Card. Fail., 21:S84 (2015).

Braunwald et al., Mechanisms of contraction of the normal and failing heart, N. Engl. J. Med., 277:1012-1022 (1967).

Bretz et al., A graphical approach to sequentially rejective multiple test procedures, Statistics in Medicine, 28:586-604 (2009).

Cleland et al., Plasma concentration of aminoterminal pro-brain natriuretic peptide in chronic heart: failure prediction of cardiovascular events and interaction with the effects of rosuvastatin: a report from CORONA (Controlled Rosuvastatin Multinational Trial in Heart Failure), J. Am. Coll. Cardiol., 54:1850-1859 (2009).

Cleland et al., Predicting the long-term effects of cardiac resynchronization therapy on mortality from baseline variables and the early response a report from the CARE-HF (Cardiac resynchronization in heart failure), Trial. J. Am. Coll. Cardiol., 52:438-445 (2008).

Cleland et al., The effects of the cardiac myosin activator, omecamtiv mecarbil, on cardiac function in systolic heart failure: a doubleblind, placebo controlled, crossover, dose-ranging phase 2 trial, Lancet, 378:676-683 (2011).

Dasgupta et al., Handbook of drug monitoring methods, Chapter 3: Analytical techniques for measuring concentrations of therapeutic drugs in biological fluids, 67-86 (2008).

Dickstein et al., ESC committee for practice guidelines (CPG), ESC guidelines for the diagnosis and treatment of acute and chronic heart failure 2008: The task force for the diagnosis and treatment of acute and chronic heart failure 2008 of the european society of cardiology, Developed in collaboration with the Heart Failure Association of the ESC (HFA) and endorsed by the european society of intensive care medicine (ESICM), Eur. Heart J., 29(19):2388-2442 (2008).

Greenberg et al., Safety and tolerability of omecamtiv mecarbil during exercise in patients with ischemic cardiomyopathy and angina, JACC Heart Fail, 3:22-29 (2015).

Greene et al., The vulnerable phase after hospitalization for heart failure, Nat. Rev. Cardiol., 12(4):220-229 (2015).

Hampton et al., Randomized study of effect of ibopamine on survival in patients with advanced severe heart failure, Second

(56) References Cited

OTHER PUBLICATIONS prospective randomised study of ibopamine on mortality and efficacy (Prime II) Investigators, Lancet., 5(349):971-977 (1997).
Hasenfuss et al., Cardiac inotropes: current agents and future directions, Eur. Heart. J., 32:1838-1845 (2011).
Haybittle, Repeated assessment of results in clinical trials of cancer treatment, Br. J. Radiol., 44(526):793-797 (1971).
Hicks et al., 2014 ACC/AHA Key data elements and definitions for cardiovascular endpoint events in clinical trials: A report of the american college of cardiology/american heart association task force on clinical data dtandards, J. Am. Coll. Cardiol., 66:403-469 (2015).
Hilfiker-Kleiner et al., Molecular mechanisms in heart failure, Focus on cardiac hypertrophy, inflammation, angiogenesis, and apotosis, J. Am. Coll. Cardiol., 48(9) (Suppl A:A56-66) (2006).
International Preliminary Report on Patentability for Corresponding International Application No. PCT/US2018/040181, dated Jan. 9, 2020.
International Search Report and Written Opinion for Corresponding International Application No. PCT/US2018/040181, dated Sep. 27, 2018, 10 pages.
Jencks et al., Rehospitalizations among patients in the medicare fee-for-service program, Engl. J. Med., 360(14):1418-1428 (2009).
Jessup et al., Heart failure, N. Engl. J. Med., 348:2007-2018 (2003).
Kang et al., Overview of therapeutic drug monitoring, Korean J. Intern. Med., 24(1):1-10 (2009).
Kannankeril et al., Usefulness of troponin I as a marker of myocardial injury after pediatric cardiac catheterization, Am. J. Cardiol., 90(10):1128-1232 (2002).
Kawashima et al., Pulmonary delivery of insulin with nebulized DL-lactide/glycolide copolymer (PLGA) nanospheres to prolong hypoglycemic effect, J. Control. Release, 62(1-2):279-287 (1999).
Klinkenberg et al., Circulating cardiac troponin T exhibits a diurnal rhythm, J. Am. Coll. Cardiol., 63:1788-1795 (2014).
Kramer et al., Quantitative evaluation of drug or device effects on ventricular remodeling as predictors of therapeutic effects on mortality in patients with heart failure and reduced ejection fraction: a meta-analytic approach, J. Am. Coll. Cardiol., 56:392-406 (2010).
Krum et al., Medical therapy for chronic heart failure, Lancet., 378(9792)713-721 (2011).
Levy et al., The seattle heart failure model: prediction of survival in heart failure, Circulation, 113(11):1424-1433 (2006).
Liu et al., Omecamtiv Mecarbil: A New Cardiac Myosin Activator for the Treatment of Heart Failure, Expert Opin. Investig. Drugs, 25(1): 117-127 (2015).
Liu et al., Pulmonary delivery of free and liposomal insulin, Pharm. Res., 10(2):228-232 (1993).
Lopez-Sendon, The heart failure epidemic, Medicographia., 33(4):363-369 (2011).
Malik et al., Cardiac myosin activation: a potential therapeutic approach for systolic heart failure, Science, 331:1439-1443 (2011).
McLlvennan et al., Outcomes in acute heart failure: 30-day readmission versus death, Curr. Heart Fail Rep. 11(4):445-452 (2014).
Mozaffarian et al., Heart disease and stroke statistics-2013 update: a report from the American heart association, Circulation, 127:e6-e245 (2013).
Mozaffarian et al., Prediction of mode of death in heart failure: the Seattle heart failure model, Circulation, 116:392-398 (2007).
Nagy et al., Inotropes and Inodilators for Acute Heart Failure: Sarcomere Active Drugs in Focus, Journal of Cardiovascular Pharmacology, 64(3):199-208, (2014).
Packer et al., Effect of oral milrinone on mortality in severe chronic heart failure, The PROMISE study research group, N. Engl. J. Med., 325(21):1468-1475 (1991).
Packer, The search for the ideal positive inotropic agent, N. Engl. J. Med., 329:201-202 (1993).
Palaparthy et al., Relative bioavailability, food effect, and safety of the single-dose pharmacokinetics of omecamtiv mecarbil following administration of different modified-release formulations in healthy subjects, Int. J. Clin. Pharmacol. Ther., 54:217-227 (2016).

Peto et al., Design and analysis of randomized clinical trials requiring prolonged observation of each patient, I. Introduction and design, Br. J. Cancer, 34(6):585-612 (1976).
Ponikowski et al., ESC Guidelines for the diagnosis and treatment of acute and chronic heart failure, Eur. Heart. J., 18(8):891-975 (2016).
Qian et al., Pulmonary delivery of a GLP-1 receptor agonist, BMS-686117, Int. J. Pharm., 366:218-220 (2009).
Qian et al., Sustained release subcutaneous delivery of BMS-686117, a GLP-1 receptor peptide agonist, via a zinc adduct, J. Pharm., 374:46-52 (2009).
Rahimi et al., Risk prediction in patients with heart failure: a systematic review and analysis, JACC Heart Fail, 2:440-446 (2014).
Shave et al., Exercise-induced cardiac troponin elevation: evidence, mechanisms, and implications, J. Am. Coll. Cardiol., 56:169-176 (2010).
Shen et al.. Improvement of cardiac function by a cardiac myosin activator in conscious dogs with systolic heart failure, Cric. Heart Fail, 3:522-527 (2010).
Shih, Sample size calculation for complex clinical trials with survival endpoints, Control Clin. Trials., 16(6):395-407 (1995).
Teerlink, J.R. et al. (2016). "Online Appendix: Acute Treatment With Omecamtiv Mecarbil to Increase Contractility in Acute Heart Failure: the ATOMIC AHF Study," J. Am. Coll. Cardiol. 67:1444-1455, Appendix, 16 pages.
U.S. Appl. No. 17/448,833, filed Sep. 24, 2021, by Sheng Cui et al. (The U.S. Patent Application is not submitted herewith pursuant to the waiver of 37 C.F.R. § 1,98(a)(2)(iii) issued by the Office on Sep. 21, 2004.).
U.S. Appl. No. 17/452,025, filed Oct. 22, 2021, by Bradley Paul Morgan et al. (The U.S. Patent Application is not submitted herewith pursuant to the waiver of 37 C.F.R. § 1,98(a)(2)(iii) issued by the Office on Sep. 21, 2004.).
U.S. Appl. No. 17/454,592, filed Nov. 11, 2021, by Narimon Honarpour et al. (The U.S. Patent Application is not submitted herewith pursuant to the waiver of 37 C.F.R. § 1,98(a)(2)(iii) issued by the Office on Sep. 21, 2004.).
U.S. Appl. No. 17/690,729, filed Mar. 9, 2022, by Caille Sebastien et al. (The U.S. Patent Application is not submitted herewith pursuant to the waiver of 37 C.F.R. § 1.98(a)(2)(iii) issued by the Office on Sep. 21, 2004.).
Anonymous (May 1, 2017). "Cytokinetics Announces Results From Dose Escalation Phase of Cosmic-HF Presented at Heart Failure 2017," Globe Newswire, 6 pages.
Anonymous (Dec. 1, 2016). "Cytokinetics Announces Start of Galactic-HF, A Phase 3 Clinical Trial of Omecamtiv Mecarbil," Globe Newswire, 6 pages.
Anonymous (Sep. 1, 2016). "Cytokinetics and Amgen to Advance Omecamtiv Mecarbil to Phase 3 Clinical Development," Globe Newswire, 6 pages.
Anonymous (Oct. 27, 2015). "Amgen and Cytokinetics Announce Positive Top-Line Results From Cosmic-HF, A Phase 2 Trial of Omecamtiv Mecarbil in Patients With Chronic Heart Failure," Globe Newswire, 11 pages.
Anonymous (Mar. 13, 2015). "Cytokinetics Announces Completion of Enrollment in Cosmic-HF," Cytokinetics, Inc., 7 pages.
Anonymous (Nov. 30, 2016). "The Lancet Publishes Results From Cosmic-HF Trial Showing Omecamtiv Mecarbil Significantly Improved Cardiac Function in Patients With Chronic Heart Failure," Globe Newswire, 13 pages.
Anonymous (Apr. 4, 2016). "Cytokinetics Announces Start of Phase 2 Clinical Trial of Omecamtiv Mecarbil in Japanese Subjects With Heart Failure," Globe Newswire, 5 pages.
clinicaltrials.gov (May 15, 2017). "History of Changes for Study NCT02695420: Safety, PK, and Efficacy of Omecamtiv Mercarbil in Japanese Subjects with Heart Failure With Reduced Ejection Fraction," 6 pages.
clinicaltrials.gov (Jun. 21, 2017). "History of Changes for Study NCT02929329: Registrational Study With Omecamtiv Mecarbil/ AMG 423 to Treat Chronic Heart Failure With Reduced Ejection Fraction (GALACTIC-HF)," 30 pages.
NCT02695420—(May 15, 2017). History of Changes of Study: Safety, PK, and Efficacy of omecamtiv mecarbil in Japanese Sub-

(56) References Cited

OTHER PUBLICATIONS jects With Heart Failure With Reduced Ejection Fraction, ClinicalTrials.gov, retrieved from the Internet <https://clinicaltrials.gov/ct2/historv/NCT02695420?A±15&B=15&C-merged#StudyPaqeTop>, last visited Jun. 22, 2022, 7 pages.

Teerlink, J.R. et al. (May 2014). "Chronic Oral Study of Myosin Activation to Increase Contractility in Heart Failure (COSMIC-HF): Improved Contractility and Evolution of Ventricular Remodelling Through Time," European Society of Cardiology—Heart Failure, 1 pages.

* cited by examiner

METHODS OF TREATING HEART FAILURE WITH CARDIAC SARCOMERE ACTIVATORS

CROSS REFERENCE TO RELATED APPLICATION

The benefit under 35 U.S.C. § 119(e) of U.S. Provisional Patent Application No. 62/527,983, filed on Jun. 30, 2017, is hereby claimed, and the disclosure thereof is hereby incorporated by reference herein.

BACKGROUND

Heart failure (HF) is a clinical syndrome defined by an imbalance between cardiac function and metabolic demands of the body. It is a final pathway for many diseases that affect the heart (Hilfiker-Kleiner et al, 2006). HF affects over 26 million people worldwide, with more than 3.5 million people newly diagnosed every year. The prevalence has been shown to increase with age (López-Sendón, 2011), suggesting that as the population ages, the incidence of HF may rise. In the United States (US), more than 5 million people, or almost 2.0% of the population, have HF (Go et al, 2013). In Europe, it has been estimated that at least 15 million people have HF (Dickstein et al, 2008). HF is typically further categorized as either "reduced" or "preserved" ejection fraction. The annual mortality rate of heart failure with reduced ejection fraction (HFrEF) patients in western industrialized countries is typically from 10% to 25% per year; however, depending on the HF severity, this rate can be as low as 5% per year in stable New York Heart Association (NYHA) class I to II patients to as high as 75% per year in patients with NYHA class III to IV disease (Mozaffarian et al, 2007; Bhatia et al, 2006; Levy et al, 2006; Solomon et al, 2004). The burden of HF can also be seen in data from recurrent hospital admission. Medicare data and data on commercially insured patients indicate that 12% to 27% of patients hospitalized for HF are readmitted within 30 days after their hospitalization, and all-cause mortality reaches 12% in the same period (Jencks et al, 2009; McIlvennan et al, 2014).

HF is most often caused by coronary artery disease (CAD); other etiologies include hypertensive heart disease, valvular heart disease and idiopathic causes (Ambrosy et al, 2014). In an attempt to preserve cardiac output and organ perfusion, HF progresses through stages with compensatory mechanisms characterized by increased sympathetic tone, peripheral vasoconstriction, and activation of various neurohormonal pathways. These adaptive properties provide short-term relief but can be damaging with long-term or prolonged activation. Patients experience dyspnea, fatigue, and fluid retention and eventually develop pulmonary congestion and peripheral edema. Treatment goals are to improve symptoms, prolong survival, and reduce hospital readmissions (Yancy et al, 2013; Ponikowski et al, 2016). While several pharmacological and nonpharmacological interventions have been shown to reduce the rate of HF hospitalizations and improve mortality, including angiotensin-converting enzyme inhibitors (ACEis), beta-blockers, aldosterone antagonists, coronary revascularization, and biventricular pacing (Jessup and Brozena, 2003; Krum and Teerlink, 2011), mortality and morbidity still remain high as noted above. In addition, these available treatments, acting on the compensatory mechanisms (eg, sodium retention, arterial and venous constriction, neuroendocrine activation, and increased heart rate) often fail to control symptoms or restore quality of life.

Reduced left ventricle ejection fraction (LVEF) is a central factor in HF, yet there are no safe medical therapies to directly improve cardiac function at the level of the cardiac sarcomere in HF patients. The compensatory mechanisms cited above are deployed in attempt to preserve cardiac output and organ perfusion in a scenario of impaired myocardial contractility. Attempts to improve cardiac contractility through chronic stimulation of the adrenergic receptor pathway (eg, dobutamine or ibopamine) or phosphodiesterase inhibitors (ie, milrinone) in chronic HF patients have not been successful (Tacon et al, 2012). Both agents have significant safety liabilities due to their mechanism of action. The increase of intracellular calcium can improve contractility but at the expense of increased tissue oxygen consumption and arrhythmias. The addition of long-term oral milrinone to SoC in severe chronic HFrEF patients has shown increased mortality and morbidity (Packer et al, 1991). Oral ibopamine, a dopaminergic receptor agonist (DA-1 and DA-2) also did not demonstrate clinical benefits when added to SoC in HFrEF outpatients (Hampton et al, 1997).

Thus, there remains a need for safe and effective methods of treating HF etiologies, including HFrEF.

SUMMARY

Provided herein are treatment methods comprising administering a cardiac sarcomere activator (CSA) at an initial dose, e.g., a starting dose, for an initial time period, and subsequently administering the CSA at a dose that is determined based on the subject's plasma concentration during or at the end of the initial time period. In exemplary embodiments, the treatment methods of the present disclosure provide an approach to treating a subject with a CSA. In exemplary embodiments, the treatment methods of the present disclosure provide an approach to individualizing treatment of a subject with a CSA. In exemplary embodiments, the treatment methods of the present disclosure provide a safe and improved way to treat subjects with heart failure, e.g., HFrEF, maximizing efficacious exposure in each individual subject, while avoiding overexposure to the CSA.

Accordingly, the present disclosure provides methods of treating a subject with heart failure. In exemplary embodiments, the method comprises (a) administering to the subject an initial dose of a cardiac sarcomere activator (CSA) for an initial time period, and (b) subsequently administering to the subject a dose of the CSA based on the subject's plasma concentration of the CSA during or at the end of the initial time period. In exemplary aspects, the initial dose is the minimum effective dose (MED) of the CSA. In exemplary aspects, the CSA has reached steady state in the subject by the end of the initial time period or by the time the plasma concentration of the CSA is determined. In exemplary aspects, the method comprises subsequently administering to the subject a dose of the CSA based on the subject's steady state plasma concentration of the CSA. In exemplary aspects, the dose that is subsequently administered to the subject is one of two options: the subsequently administered dose is either the same as the initial dose or is greater than the initial dose. In alternative or additional exemplary aspects, the dose that is subsequently administered to the subject is one of three options: the subsequently administered dose is (i) the same as the initial dose, (ii) greater than the initial dose but lower than a maximum dose, or (iii) a maximum dose. In exemplary aspects, when the subject's plasma concentration of the CSA is greater than a threshold concentration, the subsequently administered dose is the same as the initial dose. In exemplary instances, the threshold concentration is about 1.0 to about 1.5 times the minimum of a target concentration range. In exemplary aspects, when the subject's plasma concentration of the CSA is less than the threshold, the subsequently administered dose is greater than the initial dose. In exemplary instances, the threshold concentration is about 1.0 times to about 1.5 times the minimum of a target concentration range.

In exemplary embodiments, the method of treating a subject with HF comprises (a) administering to the subject an initial dose of a CSA for an initial time period, and (b) subsequently administering to the subject a dose of the CSA based on the subject's plasma concentration of the CSA during or at the end of the initial time period. In exemplary aspects, when the subject's plasma concentration of the CSA is greater than or equal to the minimum of a target concentration range, the subsequently administered dose is the same as the initial dose. In exemplary aspects, when the subject's plasma concentration of the CSA is less than the minimum of the target concentration range, the subsequently administered dose is greater than the initial dose. In exemplary aspects, when the subject's plasma concentration is greater than or about 1.5 times the minimum of a target concentration range, the subsequently administered dose is the same as the initial dose. In exemplary aspects, when the subject's plasma concentration of the CSA is less than 1.5 times the minimum of the target concentration range but greater than or about the minimum of the target concentration range, the subsequently administered dose is the greater than the initial dose but less than a maximum dose. In exemplary aspects, when the subject's plasma concentration of the CSA is less than the minimum of the target concentration range, the subsequently administered dose is the maximum dose.

Methods of determining a treatment regimen for a subject are further provided. In exemplary embodiments, the method comprises (a) administering to the subject the minimum effective dose (MED) dose of the CSA for an initial time period, wherein the CSA has reached a steady state in the subject during or by the end of the initial time period, and (b) determining the subject's plasma concentration of the CSA at the end of the initial time period. In exemplary aspects, the treatment regimen following the initial time period comprises a dose of the CSA that is either the same as the initial dose or is greater than the initial dose. In exemplary aspects, when the subject's plasma concentration of the CSA is greater than a threshold concentration, which in exemplary instances is about 1.0 to about 1.5 times the minimum of a target concentration range, the treatment regimen following the initial time period comprises a dose of the CSA that is the same as the initial dose. In exemplary aspects, when the subject's plasma concentration of the CSA is less than the threshold, which in exemplary instances is about 1.0 to about 1.5 times the minimum of a target concentration range, the treatment regimen following the initial time period comprises a dose of the CSA that is greater than the initial dose. In alternative or additional exemplary aspects, the treatment regimen following the initial time period comprises a dose that is one of three options: the subsequently administered dose is (i) the same as the initial dose, (ii) greater than the initial dose but lower than a maximum dose, or (iii) a maximum dose. In exemplary aspects, the treatment regimen following the initial time period comprises a dose of the CSA that is (i) essentially the same as the initial dose, when the plasma concentration of the CSA is greater than or about 1.5 times the minimum of the target concentration, (ii) greater than the initial dose but lower than a maximum dose, when the subject's plasma concentration of the CSA is greater than or about the minimum of the target concentration range but below about 1.5 times the minimum of the target concentration range, or (iii) a maximum dose, when the plasma concentration of the CSA is below the minimum of the target concentration range.

BRIEF DESCRIPTION OF THE DRAWINGS

FIG. 3 is a set of graphs depicting the least squares mean (SE) changes from baseline to 20 weeks in efficacy endpoints.

DETAILED DESCRIPTION

Treatment Methods

Figure 1:
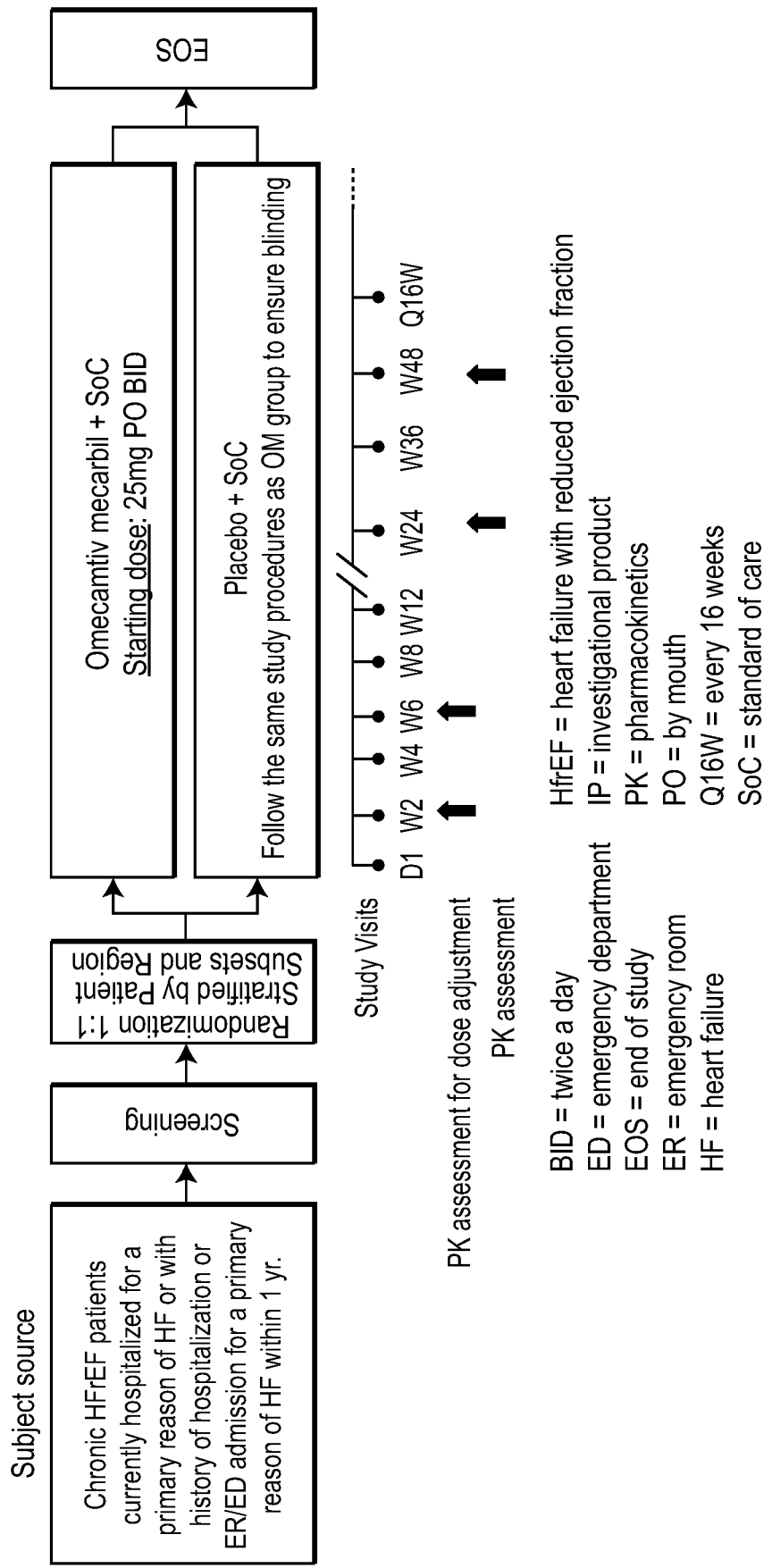
FIG. 1 is an illustration of the study design and treatment schema of the study described in Example 1.

Presented herein are data supporting treatment methods comprising administering a CSA at an initial dose, e.g., a predose, a starting dose, for an initial time period, and subsequently administering the CSA at a dose that is determined based on the subject's plasma concentration of the CSA during or at the end of the initial time period. In exemplary embodiments, the treatment methods of the present disclosure provide an approach to treating a subject with a CSA. In exemplary embodiments, the treatment methods of the present disclosure provide a safe way to treat subjects with heart failure, e.g., HFrEF, and avoid overexposure to the CSA.

Accordingly, the present disclosure provides methods of treating a subject with heart failure. In exemplary embodiments, the method comprises (a) administering to the subject an initial dose of a CSA for an initial time period, and (b) subsequently administering to the subject a dose of the CSA based on the subject's plasma concentration of the CSA at the end of the initial time period. In exemplary aspects, the initial dose is the minimum effective dose (MED) of the CSA. In exemplary aspects, the CSA has reached steady state in the subject by the end of the initial time period or by the time the plasma concentration of the CSA is determined. In exemplary aspects, the dose that is subsequently administered to the subject is one of two options: the subsequently administered dose is either the same as the initial dose or is greater than the initial dose. In alternative or additional exemplary aspects, the dose that is subsequently administered to the subject is one of three options: the subsequently administered dose is (i) the same as the initial dose, (ii) greater than the initial dose but lower than a maximum dose, or (iii) a maximum dose. In exemplary aspects, when the subject's plasma concentration of the CSA is greater than a threshold concentration, which in exemplary instances is about 1.0 to about 1.5 times the minimum of a target concentration range, the subsequently administered dose is the same as the initial dose. In exemplary aspects, when the subject's plasma concentration of the CSA is less than the threshold, which in exemplary instances is about 1.0 to about 1.5 times the minimum of a target concentration range, the subsequently administered dose is greater than the initial dose.

In exemplary aspects, the method of treating a subject with HF comprises (a) administering to the subject an initial dose of a CSA for an initial time period, and (b) subsequently administering to the subject a dose of the CSA based on the subject's plasma concentration of the CSA during or at the end of the initial time period, wherein the initial dose is a MED of the CSA and the CSA has reached steady state in the subject by the end of the initial time period or by the time the concentration of the CSA is determined. In exemplary aspects, when the subject's plasma concentration is greater than or about a threshold concentration, the subsequently administered dose is the same as the initial dose. In exemplary aspects, when the subject's plasma concentration is less than the threshold concentration, the subsequently administered dose is greater than the initial dose. In exemplary aspects, the threshold concentration is about 1.0 times to about 1.5 times the minimum of a target concentration range. In exemplary aspects, the threshold concentration is about 1.0 times the minimum of a target concentration range. In exemplary aspects, the subsequently administered dose is (i) the same as the initial dose, when the subject's plasma concentration is greater than or about a first threshold concentration, (ii) greater than the initial dose but lower than a maximum dose, when the subject's plasma concentration is below the first threshold concentration but greater than or about a second threshold concentration, or (iii) a maximum dose, when subject's plasma concentration is less than the second threshold concentration. In exemplary aspects, the first threshold concentration is about 1.5× the minimum of a target concentration range. In exemplary aspects, the second threshold concentration is the minimum of a target concentration range.

In exemplary aspects, when the subject's plasma concentration is greater than or about 1.5× the minimum of a target concentration range, the subsequently administered dose is the same as the initial dose. In exemplary aspects, when the subject's plasma concentration is less than 1.5 times the minimum of the target concentration range but greater than or about the minimum of the target concentration range, the subsequently administered dose is the greater than the initial dose but less than a maximum dose. In exemplary aspects, when the subject's plasma concentration is less than the minimum of the target concentration range, the subsequently administered dose is the maximum dose.

Heart Failure

The treatment methods of the present disclosure are methods of treating heart failure (HF). HF is defined as the inability of the heart to supply sufficient blood flow to meet the body's needs. Heart failure may be classified according to the New York Heart Association (NYHA) class system of heart failure, summarized in the table below.

| NYHA Class | Symptoms |
| --- | --- |
| I | No symptoms and no limitation in ordinary physical activity, e.g. shortness of breath when walking, climbing stairs etc. |
| II | Mild symptoms (mild shortness of breath and/or angina) and slight limitation during ordinary activity. |
| III | Marked limitation in activity due to symptoms, even during less-than-ordinary activity, e.g. walking short distances (20-100 m). Comfortable only at rest. |
| IV | Severe limitations. Experiences symptoms even while at rest. Mostly bedbound patients. |

Heart failure can be a systolic heart failure (a.k.a. systolic failure), which is heart failure caused or characterized by a systolic dysfunction. In simple terms, systolic dysfunction is a condition in which the pump function or contraction of the heart (i.e., systole), is reduced. The left ventricle loses the ability to contract normally and therefore the heart cannot pump with enough force to push enough blood into circulation. Systolic dysfunction may be characterized by a decreased or reduced ejection fraction, e.g., an ejection fraction which is less than about 45%, and an increased ventricular end-diastolic pressure and volume. Hence, in some instances, systolic heart failure is called heart failure with reduced ejection fraction (HFrEF). In exemplary instances, the systolic dysfunction is characterized by the left ventricular ejection fraction being about 40% or lower. In some aspects, the strength of ventricular contraction is weakened and insufficient for ejecting enough blood during each heartbeat, resulting in less cardiac output, as measured by the amount of blood pumped per minute. Systolic heart failure may result from ischemic heart disease, or alternatively, may result from non-ischemic heart causes.

HFrEF may be a chronic condition and is sometimes called chronic heart failure (CHF). In exemplary aspects, the subject has had heart failure for 4 weeks or more while receiving standard of care (SOC) for HF. Alternatively, heart failure may be an acute condition, i.e., may be acute heart failure. In exemplary aspects, the subject has had heart failure for less than 4 weeks while receiving standard of care (SOC) for HF.

The signs and symptoms of heart failure include dyspnea (e.g., orthopnea, paroxysmal nocturnal dyspnea), coughing, cardiac asthma, wheezing, dizziness, confusion, cool extremities at rest, pulmonary congestion, chronic venous congestion, ankle swelling, peripheral edema or anasarca, nocturia, ascites, heptomegaly, jaundice, coagulopathy, fatigue, exercise intolerance, jugular venous distension, pulmonary rales, peripheral edema, pulmonary vascular redistribution, interstitial edema, pleural effusions, fluid retention, or a combination thereof. Other signs and symptoms of HF include compensatory mechanisms characterized by increased sympathetic tone, peripheral vasoconstriction, activation of various neurohormonal pathways, sodium retention, arterial and venous constriction, neuroendocrine activation, and increased heart rate.

For purposes herein, the presently disclosed methods of treating a subject with heart failure encompass methods of treating subjects with any of the HF types described herein, e.g., HFrEF, CHF. The term "treat," as well as words related thereto, do not necessarily imply 100% or complete treatment. Rather, there are varying degrees of treatment which one of ordinary skill in the art recognizes as having a potential benefit or therapeutic effect. In this respect, the methods of treating a subject with HF of the present disclosure can provide any amount or any level of treatment. Furthermore, the treatment provided by the method of the present disclosure may include treatment of one or more conditions or symptoms or signs of the HF being treated. Also, the treatment provided by the methods of the present disclosure may encompass slowing the progression of HF. For example, the methods can treat HF by virtue of increasing the ejection fraction, increasing the strength of ventricular contraction, increasing cardiac output or blood flow into circulation, and the like.

Subjects

In some embodiments of the present disclosure, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human.

In exemplary aspects, the human is a male or female, e.g., a male or female 18 years old or older. In exemplary aspects, the subject has a confirmed diagnosis of HF, e.g., systolic heart failure, HFrEF, CHF. In exemplary aspects, the subject has chronic heart failure or a history of chronic HF. In exemplary aspects, the subject is one that requires HF treatment for at least 30 days prior to receiving the treatment with a CSA. In exemplary aspects, the subject is one has been hospitalized for HF as the primary reason for hospitalization within one year prior to receiving the CSA treatment. In exemplary aspects, the subject has a NYHA Class II or Class III or Class IV heart failure. In exemplary instances, the subject has a left ventricular ejection fraction of about 35% or less. In exemplary aspects, the subject has a B-type natriuretic peptide (BNP) level greater than or about 125 pg/mL or an NT-proBNP level greater than or about 400 pg/mL. In exemplary aspects, the subject is receiving an angiotensin receptor-neprilysin inhibitor [ARNi] and has an NT-proBNP level greater than or about 400 pg/mL In exemplary instances, the subject has atrial fibrillation and has a BNP level that is greater than or about 375 pg/mL or an NT-proBNP level that is greater than or about 1200 pg/mL. In exemplary aspects, the subject meets one or more or all of the inclusion criteria outlined here in Example 2. In exemplary aspects, the subject meets one or more or all of the exclusion criteria outlined here in Example 2. In exemplary aspects, the subject is in need of a CSA. In exemplary aspects, the subject has chronic, severe disease that is symptomatic, recently required acute care (e.g., recent hospitalization or emergency room (ER) visit) and has biomarker evidence of advanced disease (e.g., BNP).

In exemplary aspects, the human is a male or female under the age of 18 years. In exemplary aspects, the human is 6 years old or older and less than 18 years old.

Cardiac Sarcomere Activators

The presently disclosed methods comprise administration of a cardiac sarcomere activator. As used herein, the term "cardiac sarcomere activator" or "CSA" refers to an agent that induces the activation of cardiac sarcomeres by, e.g., sensitizing cardiac myofilaments to $Ca^{2+}$, activating troponin or tropomyosin, or directly activating the cardiac myosin. In exemplary instances, the CSA promotes sarcomere responsiveness to calcium ($Ca^{2+}$). For example, CSAs that promote sarcomere responsiveness to calcium include levosimendan or pimobendan. In exemplary aspects, the CSA is a drug with an added effect on myofilaments, such as, e.g., SR-33805, an HNO donor, CXL-1020.

In exemplary aspects, the CSA directly reacts with myosin and/or stabilizes the pre-powerstroke conformation of myosin facilitating the transition to the acti-bound state. In exemplary aspects, the CSA is an activator of cardiac myosin. In exemplary instances, the activator of cardiac myosin is omecamtiv mecarbil. In exemplary aspects, the CSA targets one or more of myosin, actin, troponin, and tropomyosin. In exemplary aspects, the CSA activates one or more of myosin, actin, troponin, and tropomyosin.

Omecamtiv Mecarbil (OM)

In exemplary aspects, the methods comprise administration of omecamtiv mecarbil (OM)) or a pharmaceutically acceptable salt thereof, or a solvate of any of the foregoing. The molecular formula of the free base of OM is $C_{20}H_{24}FN5O_3$ and the chemical structure is shown below:

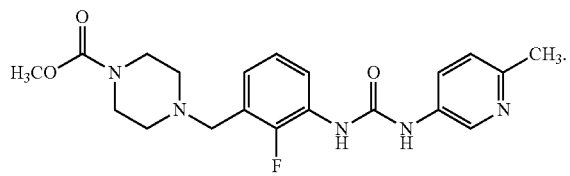 [SMILES: COC(=O)N1CCN(Cc2cccc(NC(=O)Nc3ccc(C)nc3)c2F)CC1]

It is understood and described that reference to "omecamtiv mecarbil" or "OM" refers to and describes any form of OM, including the free base, any pharmaceutically acceptable salt thereof, any solvate of any of the foregoing, and mixtures thereof in any ratio. In one embodiment, OM is administered to a subject as a free base. In some embodiments, OM is administered to a subject as a hydrochloride salt, such as a dihydrochloride salt. In some embodiments, OM is administered to a subject as a hydrate. In some embodiments, OM is administered to a subject as a salt hydrate. In some embodiments, OM is administered to a subject as a dihydrochloride hydrate.

OM (also known as AMG 423, CK-1827452) is a novel small molecule classified as a cardiac myosin activator that increases cardiac contractility by selectively and directly activating the enzymatic domain of the cardiac myosin heavy chain, the force-generating motor protein of the cardiac sarcomere, without increasing cardiac myocyte intracellular calcium (Teerlink et al, 2011; Malik et al, 2011). OM increases the left ventricular systolic ejection time (SET) without changing the velocity of contraction (dP/dt) or increasing the heart rate. Additionally, left ventricular filling pressures, left atrial pressures, and total peripheral vascular resistance decreased, providing evidence that prolongation of SET and increased systolic function can favorably impact the hemodynamics that drive HF symptoms. The salutary effects of OM were achieved without noticeable effect upon myocardial oxygen uptake, blood pressure, or coronary blood flow (Shen et al, 2010; Malik et al, 2011).

The completed omecamtiv mecarbil clinical program comprises 10 phase 1 studies, 4 phase 2a studies in subjects with chronic heart failure, 1 phase 2b study in subjects with acute heart failure (AHF), and 1 phase 2 study in subjects with chronic stable heart failure. In these studies, the efficacy, safety, tolerability, PK, and PD of omecamtiv mecarbil were evaluated with intravenous (IV) infusions up to 72 hours and oral dosing up to 20 weeks.

To date, 1097 subjects have received at least 1 dose of omecamtiv mecarbil treatment across 16 studies. This includes 278 healthy volunteers in phase 1 studies, 147 subjects with HF in phase 2a studies, 303 subjects with AHF in the phase 2b study (IV formulation), and 369 subjects with chronic HF in the phase 2b study (modified release [MR] formulation).

There are 2 ongoing clinical studies: A phase 2b, double-blind, randomized, placebo-controlled study to evaluate the safety, PK, and efficacy of omecamtiv mecarbil in Japanese subjects with chronic heart failure with reduced ejection fraction (HFrEF) and a phase 3, double-blind, randomized, placebo-controlled study to assess the efficacy and safety of omecamtiv mecarbil on mortality and morbidity in subjects with HFrEF.

The recently completed phase 2b study in subjects with chronic HF (COSMIC-HF) is the most comprehensive and relevant clinical dataset to support the phase 3 outcomes study. COSMIC-HF was designed to evaluate MR formulations of omecamtiv mecarbil in subjects with chronic HFrEF and was conducted in 2 phases: 1) the dose-escalation phase was designed to choose an oral MR formulation and dose of omecamtiv mecarbil for further evaluation in the subsequent expansion phase; 2) the expansion phase, during which the PK, PD, safety, and tolerability of the selected MR formulation and dose in subjects with chronic HF and left ventricular systolic dysfunction were evaluated over a 20-week treatment period.

Clinical studies on OM are described, e.g., in Teerlink et al, 2011; and Cleland et al, 2011, each of which is incorporated by reference in its entirety.

Dosages

As used herein, the term "dose" refers to a measured quantity of a therapeutic agent to be taken at one time. For purposes of the present disclosure, the amount or dose of the CSA administered to the subject should be sufficient to effect, e.g., a therapeutic response, in the subject or animal over a reasonable time frame. For example, the dose of the CSA should be sufficient to treat HF as described herein in a period of from about 1 to 4 minutes, 1 to 4 hours or 1 to 4 weeks or longer, e.g., 5 to 20 or more weeks, from the time of administration. In certain embodiments, the time period could be even longer. The dose may be determined by the efficacy of the particular CSA and the condition of the animal (e.g., human), as well as the body weight of the animal (e.g., human) to be treated.

Many assays for determining an administered dose are known in the art. For purposes herein, an assay that comprises comparing the extent to which HF is treated upon administration of a given dose of the CSA to a mammal among a set of mammals, each set of which is given a different dose of the CSA, could be used to determine a starting dose to be administered to a mammal. The extent to which HF is treated upon administration of a certain dose can be represented by, for example, the extent to which ejection fraction is increased through the action of the CSA in a mouse model of HFrEF. Methods of measuring ejection fraction are known in the art. See, the examples set forth herein.

The dose may also be determined based on the existence, nature and extent of any adverse side effects that might accompany the administration of a particular CSA. Typically, the attending physician will decide the dosage with which to treat each individual patient, taking into consideration a variety of factors, such as age, body weight, general health, diet, sex, therapeutic agents to be administered, route of administration, existing clinical data, product labeling, and the severity of the condition being treated.

Initial Doses and Initial Time Periods

In the methods of the present disclosure, an initial dose of the CSA is administered to the subject. In exemplary aspects, the initial dose is the minimum effective dose (MED) of the CSA. As used herein, the "minimum effective dose" or "MED" is the lowest dose of the CSA that provides a measurable change in cardiac function, e.g., as determined across a population of subjects, which is also statistically significantly superior to the response provided by a placebo. In exemplary aspects, the MED is the minimum of the therapeutic window of the CSA. The therapeutic window, also known as the pharmaceutical window, of a drug is the range of drug dosages that can treat disease effectively without having toxic effects. In exemplary aspects, the initial dose is the lowest dose at which evidence of efficacy is detectable. In exemplary aspects, the initial dose is the MED as determined in a clinical trial with human subjects and the MED is the lowest dose at which evidence of efficacy is detectable in greater than about 50% of the subjects participating in the clinical trial. In exemplary aspects, the initial dose is the MED as determined in a clinical trial with human subjects and the MED is the lowest dose at which evidence of efficacy is detectable in greater than about 60%, greater than about 70%, greater than about 80%, greater than about 90%, or greater than about 95% of the subjects participating in the clinical trial.

In exemplary aspects, the initial dose of the CSA is administered to the subject for an initial time period. In exemplary aspects, the initial dose of the CSA is repeatedly administered to the subject during the initial time period. In exemplary aspects, the initial dose of the CSA is repeatedly administered to the subject during the initial time period and each initial dose is the same amount of the CSA. In exemplary aspects, the CSA has reached a steady state in the subject by the end of the initial time period or by an earlier time that is during the initial time period. By "steady state" is meant the instance in which the overall intake of the drug is in dynamic equilibrium with its elimination. In exemplary aspects, the initial time period is at least 3 days, at least 4 days, at least 5 days, at least 6 days, or about 1 week. In exemplary aspects, the initial time period is more than about 1 week, e.g., about 1.5 weeks, about 2 weeks, about 3 weeks, about 4 weeks, or about 1 month. In exemplary aspects, the initial time period is more than 1 month, e.g., about 1.5 months, about 2 months, or about 3 months, or longer. In exemplary aspects, the initial time period is at least about 1 week or at least about 2 weeks. In exemplary aspects, the initial time period is about 1 week to about 3 weeks or about 2 weeks.

In exemplary aspects, the initial dose of the CSA is about 20 mg to about 30 mg or about 22.5 mg to about 27.5 mg. For example, the initial dose, is about 20 mg, about 21 mg, about 22 mg, about 23 mg, about 24 mg, about 25 mg, about 26 mg, about 27 mg, about 28 mg, about 29 mg, or about 30 mg. In exemplary aspects, the initial dose is about 25 mg. In exemplary aspects, the initial dose, e.g., 25 mg, is taken twice a day. In exemplary aspects, the initial dose is administered to the subject orally. In exemplary aspects, the CSA is OM.

In exemplary aspects, the CSA is OM and the initial dose is 25 mg OM. In exemplary aspects, the method comprises administering to the subject an initial dose of 25 mg OM via oral administration. In exemplary aspects, the method comprises administering to the subject an initial dose of 25 mg OM twice daily. In exemplary instances, the initial time period is at least about 2 weeks. In exemplary aspects, the method comprise administering to the subject about 25 mg OM twice daily via oral administration for at least about 2 weeks.

Subsequent Doses

In exemplary embodiments of the methods of the present disclosure, a dose of the CSA is administered to the subject subsequent to the initial time period, which dose is based on the subject's plasma concentration of the CSA during or at the end of the initial time period. In exemplary aspects, the dose administered subsequent to the initial time period depends on the plasma concentration of the CSA and where it falls relative to a target concentration range for the CSA. As used herein, the term "target concentration range" is synonymous with "therapeutic range" referenced in Korean J Intern Med 24(1): 1-10 (2009) and refers to the range of plasma concentrations of a drug within which a therapeutic response can be expected.

In exemplary aspects, the dose that is subsequently administered to the subject is one of two options: the subsequently administered dose is either the same as the initial dose or is greater than the initial dose. In alternative or additional exemplary aspects, the dose that is subsequently administered to the subject is one of three options: the subsequently administered dose is (i) about the same as the initial dose, (ii) greater than the initial dose but lower than a maximum dose, or (iii) a maximum dose. In yet other embodiments, the dose that is subsequently administered to the subject is one of four or more options: the subsequently administered dose is (i) about the same as the initial dose (ii) one of two or more non-equal doses that are each greater than the initial dose but lower than a maximum dose, or (iii) a maximum dose. In exemplary aspects, when the subject's plasma concentration of the CSA is greater than a threshold concentration, the subsequently administered dose is the same as the initial dose. In exemplary instances, the threshold concentration is about 1.0 to about 1.5 (e.g., about 1.0, about 1.1., about 1.2, about 1.3, about 1.4, about 1.5) times the minimum of a target concentration range. In exemplary aspects, when the subject's plasma concentration is less than the threshold, the subsequently administered dose is greater than the initial dose.

In exemplary aspects, the maximum dose is the maximum of the therapeutic window of the CSA. The therapeutic window, also known as the pharmaceutical window, of a drug is the range of drug dosages which can treat disease effectively without having toxic effects. In exemplary aspects, the maximum dose is the maximum tolerated dose (MTD). In exemplary aspects, the maximum dose is the MTD as determined in a clinical trial with humans and the MTD is the maximum dose tolerated by greater than about 50% of the subjects participating in the clinical trial. In exemplary aspects, the maximum dose is the MTD as determined in a clinical trial with humans and the MTD is the maximum dose tolerated by greater than about 60%, greater than about 70%, greater than about 80%, greater than about 90%, or greater than about 95% of the subjects participating in the clinical trial.

In exemplary aspects, when the subject's plasma concentration of the CSA is greater than or about a threshold concentration, the subsequently administered dose is the same as the initial dose. In exemplary aspects, when the subject's plasma concentration of the CSA is less than the threshold concentration, the subsequently administered dose is greater than the initial dose. In exemplary aspects, the threshold concentration is about 1.0 times to about 1.5 (e.g., about 1.0, about 1.1., about 1.2, about 1.3, about 1.4, about 1.5) times the minimum of a target concentration range. In exemplary aspects, the threshold concentration is the minimum of a target concentration range. In exemplary aspects, when the subject's plasma concentration of the CSA is greater than or about the minimum of a target concentration range, the subsequently administered dose is about the same as the initial dose, and when the subject's plasma concentration of the CSA is less than the minimum of the target concentration range, the subsequently administered dose is greater than the initial dose.

In exemplary aspects, the subsequently administered dose of the CSA is based on the subject's plasma concentration of the CSA relative to a first threshold and a second threshold. In exemplary aspects, the first threshold concentration is about 1.5 times the minimum of a target concentration range and the second threshold concentration is the minimum of a target concentration range. In exemplary aspects, the subsequently administered dose is (i) the same as the initial dose, when the subject's plasma concentration of the CSA is greater than or about a first threshold concentration, (ii) greater than the initial dose but lower than a maximum dose, when the subject's plasma concentration of the CSA is below the first threshold concentration but greater than or about a second threshold concentration, or (iii) a maximum dose, when subject's plasma concentration of the CSA is less than the second threshold concentration.

In exemplary aspects, the minimum of the target concentration range is 200 ng/mL, such that, when the subject's plasma concentration of the CSA is greater than or about 300 ng/mL, the subsequently administered dose is the same as the initial dose. In exemplary aspects, when the subject's plasma concentration of the CSA is less than 300 ng/mL but greater than or about 200 ng/mL, the subsequently administered dose is greater than the initial dose but less than a maximum dose. In exemplary aspects, when the subject's plasma concentration of the CSA is less than 200 ng/mL, the subsequently administered dose is the maximum dose. In exemplary aspects, the maximum dose is about twice the initial dose and the dose that is greater than the initial dose but less than a maximum dose is 1.5 times the initial dose. In exemplary aspects, the initial dose is about 20 mg to about 30 mg, optionally, about 25 mg. In exemplary aspects, the maximum dose is about 45 mg to about 55 mg, optionally, about 50 mg. In exemplary aspects, the dose that is greater than the initial dose but less than a maximum dose is about 35 mg to about 40 mg, optionally, about 37.5 mg.

In exemplary aspects, the initial dose is about 20 mg to about 30 mg, and the dose administered subsequent to the initial time period is (a) about 45 mg to about 75 mg, when the plasma concentration of the CSA during or at the end of the time period is less than the minimum of a target concentration range, (b) about 30 mg and less than about 45 mg, when the plasma concentration of the CSA during or at the end of the time period is greater than or about the minimum of a target concentration range but less than about 1.5 times the minimum of the target concentration range, or (c) about the same as the initial dose, when the plasma concentration of the CSA during or at the end of the time period is, for example, greater than or about to ~1.5 times the minimum of the target concentration. In exemplary aspects, the subsequent dose is about 45 mg to about 55 mg, optionally, about 50 mg, when the plasma concentration of the CSA during or at the end of the time period is less than the minimum of a target concentration range. In exemplary aspects, when the plasma concentration of the CSA during or at the end of the time period is greater than or equal to the minimum of a target concentration range but less than 1.5× the minimum of the target concentration range, the subsequent dose is about 35 mg to about 40 mg, optionally, about 37.5 mg.

In exemplary aspects, the target concentration range of the CSA is about 200 ng/mL to about 1200 ng/mL, optionally, about 200 ng/mL to about 1000 ng/mL. In exemplary aspects, the target concentration range is about 200 ng/mL to about 1000 ng/mL, the initial dose is about 25 mg, the maximum dose is about 50 mg, and the dose that is less than the maximum dose but greater than the initial dose is about 37.5 mg. In exemplary aspects, the subsequent dose is about 25 mg, when the plasma concentration of the CSA is greater than or about 300 ng/mL, the subsequent dose is about 50 mg, when the plasma concentration of the CSA is less than about 200 ng/mL, and the subsequent dose is 37.5 mg, when the plasma concentration of the CSA is greater than or about 200 ng/mL but less than 300 ng/mL. In exemplary aspects, the CSA is OM, and, optionally, OM is administered to the subject twice daily via oral administration.

In exemplary embodiments, the treatment method comprises administering only one initial dose and/or only one subsequent dose. In alternative embodiments, the method comprises administering more than one initial dose and/or more than one subsequent dose. In exemplary aspects, the method comprises repeatedly administering the initial dose during the initial time period and each initial dose is the same amount, e.g., about 25 mg. In exemplary aspects, the method comprises administering to the subject the initial dose daily, twice daily, 3 times daily, 4 times daily or more for the duration of the initial time period, optionally, at least or about 2 weeks. In exemplary aspects, the method comprises administering to the subject the initial dose weekly, twice weekly, 3 times weekly, 4 times weekly, 5 times weekly, or more for the duration of the initial time period, optionally, at least or about 2 months. In exemplary aspects, the method comprises repeatedly administering the subsequent dose after the initial time period and each subsequent dose is the same amount, e.g., about 25 mg, about 37.5 mg, about 50 mg, provided that the subsequent dose is based on the subject's plasma concentration of the CSA during or at the end of the initial time period. In exemplary aspects, the dose of the CSA is repeatedly administered to the subject after the initial time period for at least about 1 week, at least about 2 weeks, at least about 3 weeks, at least about 4 weeks, at least about 5 weeks, at least about 6 weeks, at least about 7 weeks, at least about 8 weeks, or longer. In exemplary aspects, the method comprises administering to the subject the subsequent dose daily, twice daily, 3 times daily, 4 times daily or more. In exemplary aspects, the method comprises administering to the subject the subsequent dose weekly, twice weekly, 3 times weekly, 4 times weekly, 5 times weekly, or more. In exemplary aspects, the frequency at which the initial doses are administered during the initial time period is the same frequency at which the subsequent doses are administered after the initial time period. In exemplary aspects, the subsequent dose is administered twice daily for at least about 1 week, at least about 2 weeks, at least about 3 weeks, at least about 4 weeks, at least about 5 weeks, at least about 6 weeks, at least about 7 weeks, at least about 8 weeks, or longer. In exemplary aspects, the subsequent dose is administered via oral administration.

In exemplary aspects, the CSA is OM and subsequent doses of OM are administered to the subject twice daily via oral administration, wherein each subsequent dose is about 50 mg, when the plasma concentration of OM is less than about 200 ng/mL, each subsequent dose is about 37.5 mg, when the plasma concentration of OM is greater than or equal to about 200 ng/mL but less than 300 ng/mL, and each subsequent dose is about 25 mg, when the plasma concentration of OM is greater than or about 300 ng/mL and less than 1000 ng/mL.

Formulations, Routes of Administration and Regimen

In exemplary aspects, the CSA is present in a pharmaceutical composition at a purity level suitable for administration to a patient. In some embodiments, the CSA has a purity level of at least about 90%, about 91%, about 92%, about 93%, about 94%, about 95%, about 96%, about 97%, about 98% or about 99%, and a pharmaceutically acceptable diluent, carrier or excipient. The pharmaceutical composition in some aspects comprises the CSA at a concentration of at least A, wherein A is about 10 mg, about 15 mg, about 20 mg, about 21 mg, about 22 mg, about 23 mg, about 24 mg, about 25 mg or higher. In some embodiments, the pharmaceutical composition comprises the CSA at a concentration of at most B, wherein B is about 100 mg, about 75 mg, about 50 mg, or 25 mg. In some embodiments, the compositions may contain a CSA at a concentration range of A to B mg/ml, for example, about 0.001 mg to about 100.0 mg. In exemplary aspects, the pharmaceutical composition comprises the CSA at a concentration of 25 mg, 37.5, or 50 mg.

Depending on the route of administration, the particular CSA intended for use, as well as other factors, the pharmaceutical composition may comprise additional pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface CSAs, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

Accordingly, in some embodiments, the pharmaceutical composition comprises any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, ☐-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC)chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edentate, disodium edentate, disodium hydrogen phosphate, docusate calcium, docusate potassium, docusate sodium, dodecyl gallate, dodecyltrimethylammonium bromide, edentate calcium disodium, edtic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil, type II, hydroxyethyl cellulose, 2-hydroxyethyl-β-cyclodextrin, hydroxypropyl cellulose, low-substituted hydroxypropyl cellulose, 2-hydroxypropyl-β-cyclodextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium trisilicate, magnesium trisilicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, postassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), theobroma oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type I hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the Handbook of Pharmaceutical Excipients, Third Edition, A. H. Kibbe (Pharmaceutical Press, London, U K, 2000), which is incorporated by reference in its entirety. Remington's Pharmaceutical Sciences, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the pharmaceutical compositions, its use in pharmaceutical compositions is contemplated. Supplementary active ingredients also can be incorporated into the compositions.

In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiological compatible pH. The buffering agents may include any compounds capabale of buffering at the desired pH such as, for example, phosphate buffers (e.g., PBS), triethanolamine, Tris, bicine, TAPS, tricine, HEPES, TES, MOPS, PIPES, cacodylate, MES, and others. In certain embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g., at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM).

The CSA or a pharmaceutical composition comprising the same, may be administered to the subject via any suitable route of administration. The following discussion on routes of administration is merely provided to illustrate exemplary embodiments and should not be construed as limiting the scope in any way.

Formulations suitable for oral administration can consist of (a) liquid solutions, such as an effective amount of the CSA of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the active agent of the present disclosure in a flavor, usually sucrose and acacia or tragacanth, as well as pastilles comprising the CSA of the present disclosure in an inert base, such as gelatin and glycerin, or sucrose and acacia, emulsions, gels, and the like containing, in addition to, such excipients as are known in the art.

The CSAs of the present disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa. In some embodiments, the CSA is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The CSA of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-I53-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-3-aminopropionates, and 2-alkyl-imidazoline quaternary ammonium salts, and (e) mixtures thereof.

The parenteral formulations in some embodiments contain from about 0.5% to about 25% by weight of the CSA of the present disclosure in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

Injectable formulations are in accordance with the present disclosure. The requirements for effective pharmaceutical carriers for injectable compositions are well-known to those of ordinary skill in the art (see, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986)).

It will be appreciated by one of skill in the art that, in addition to the above-described pharmaceutical compositions, the CSA of the disclosure can be formulated as inclusion complexes, such as cyclodextrin inclusion complexes, or liposomes.

In some embodiments, the CSAs described herein can be modified into a depot form, such that the manner in which the CSA of the present disclosure is released into the body to which it is administered is controlled with respect to time and location within the body (see, for example, U.S. Pat. No. 4,450,150). Depot forms of CSAs of the present disclosure can be, for example, an implantable composition comprising the CSAs and a porous or non-porous material, such as a polymer, wherein the CSA is encapsulated by or diffused throughout the material and/or degradation of the non-porous material. The depot is then implanted into the desired location within the body of the subject and the CSA is released from the implant at a predetermined rate. The pharmaceutical composition comprising the CSA in certain aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., J Pharm 374: 46-52 (2009) and International Patent Application Publication Nos. WO 2008/130158, WO2004/033036; WO2000/032218; and WO 1999/040942. In exemplary aspects, the pharmaceutical composition is a modified release formulation and not an immediate release formulation. In exemplary aspects, the modified release formulation has a $C_{max}$ or the maximum observed plasma concentration or about 175 to about 210 ng/mL for a 25 mg dose and a $C_{max}$ of about 475 ng/mL to about 510 ng/mL for a 50 mg dose, a $T_{max}$ or time to $C_{max}$ of about 2 hours to about 5 hours for a 25 mg dose, and a $T_{max}$ of about 2 hours to 3 hours for a 50 mg dose.

In exemplary aspects, the CSA is administered to the subject according to a treatment regimen. In exemplary aspects, the CSA is administered to the subject once daily, twice daily, three times daily, four times daily, once every 2 days, once every 3 days, once every 4 days, once every 5 days, once every 6 days, once a week, once every two weeks, once every 3 weeks, or once a month. In exemplary aspects, the CSA is administered to the subject twice daily via oral administration.

Plasma Concentration

In exemplary embodiments of the method of the present disclosure, a dose of the CSA based on the subject's plasma concentration of the CSA is subsequently administered to the subject during or after the initial time period. In exemplary aspects, the dose that is subsequently administered after the initial time period is based on the subject's plasma concentration measured or determined during the initial time period. In exemplary aspects, the initial time period is about 2 weeks, about 3 weeks, about 4 weeks, about 5 weeks, about 6 weeks, or longer. For example, if the initial time period is about 4 weeks, then the subject's plasma concentration is measured at a timepoint within that 4 week period. In exemplary instances, the subject's plasma concentration is measured at about 1 week, about 2 weeks, or about 3 weeks after the first administration of the initial dose. In exemplary embodiments of the methods of the present disclosure, the method comprises determining the plasma concentration of the CSA at the end of the initial time period, e.g., at 4 weeks if the initial time period is 4 weeks.

In exemplary embodiments of the methods of the present disclosure, the method comprises a step of determining or measuring the subject's plasma concentration of the CSA. In exemplary aspects, the determining or measuring step occurs at about 1 week, about 2 weeks, or about 3 weeks after the first administration of the initial dose or at the end of the initial time period, e.g., at about 4 weeks.

In exemplary embodiments, the subject's plasma concentration of the CSA is measured more than one time, e.g., two times, three times, four times, or more, every 2 weeks, every 3 weeks, every 4 weeks, every 5 weeks, every 6 weeks, every 7 weeks, every 8 weeks. In exemplary instances, the method comprises a step of determining a first plasma concentration of the CSA after the initial time period and determining a second plasma concentration following administering to the subject at least one subsequent dose of the CSA after the initial time period.

In exemplary aspects, the subject's plasma concentration of the CSA is measured during the initial time period and then about 4 weeks thereafter. In exemplary aspects, the subject's plasma concentration of the CSA is measured at about 2 weeks after the first administration of the initial dose and then again at about 6 weeks after the first administration of the initial dose.

For purposes herein, the plasma concentration of the CSA may be determined using any method known in the art. Suitable methods of determining a plasma concentration of a drug known in the art, include, for example, gas chromatography (GC), high performance liquid chromatography (HPLC), high-performance liquid chromatography-mass spectroscopy (HPLC-MS), liquid chromatography mass spectroscopy (LCMS), immunoassays (e.g., competition immunoassays, immunometric immunoassays, fluorescence polarization immunoassay (FPIA), enzyme immunoassay (EMIT), and enzyme-linked immunosorbant assay (ELISA)), or a combination thereof. See, e.g., Wang et al., Nan Fan Yi Ke Da Xue Xue Bao 28(11): 1993-1995 (2008); Dasgupta and Datta, Handbook of Drug Monitoring Methods, Chapter 3: Analytical Techniques for Measuring Concentrations of Therapeutic Drugs in Biological Fluids, Pages 67-86 (2008); Kang and Lee, Korean J Intern Med 24(1): 1-10 (2009); Glazko, Antiepileptic Drugs, $3^{rd}$, ed., New York: Raven Press, 1989, Pgs 159-176; and Steijns et al., Ther Drug Monit 24: 432-435 (2002). In exemplary aspects, the method comprises determining the plasma concentration by performing LC-MS/MS or a quantitative microsphere assay. In exemplary aspects, the method comprises determining plasma concentration by a competitive inhibition immunoassay in which free-drug in the plasma sample competes for antibody binding sites with drug molecules coated onto uniform microparticles. In exemplary aspects, the plasma concentration of the CSA is determined using the QMS™ Therapeutic Drug Monitoring (TDM) Assay, CEDIA™ Therapeutic Drug Monitoring (TDM) Assay or the DRI™ TDM Assay (ThermoFisher Scientific, Waltham, Mass.).

In exemplary aspects, the plasma concentration of the CSA is determined by measurement of the CSA in the plasma of the subject. In alternative aspects, the plasma concentration of the CSA is determined by measurement of a metabolite of the CSA in the plasma of the subject. In exemplary aspects, the plasma concentration of the CSA is a trough CSA concentration in plasma. In exemplary aspects, the plasma concentration of the CSA is determined at the beginning of the day and/or before a first dose is administered to the subject.

EXEMPLARY EMBODIMENTS

In exemplary aspects, the activator of cardiac myosin is OM and the method comprises repeatedly administering to the subject an initial dose of OM twice a day for at least or about 2 weeks, wherein each initial dose is about 25 mg administered via oral administration. In exemplary aspects, the therapeutic concentration range is about 200 ng/mL to about 1000 ng/mL, the method comprises repeatedly administering subsequent doses to the subject twice daily via oral administration, wherein the subsequent dose is (i) about 25 mg, when the plasma concentration of the CSA is greater than or about 300 ng/mL but less than about 1000 ng/mL, (ii) about 37.5 mg, when the plasma concentration of the CSA is greater than or about 200 ng/mL but less than about 300 ng/mL, or (iii) about 50 mg, when the plasma concentration of the CSA is less than about 200 ng/mL. In alternative aspects, the subsequent dose is administered to the subject twice daily and/or is orally administered to the subject, and the subsequent dose is (i) about 25 mg, when the plasma concentration of the CSA is greater than or about 200 ng/mL but less than about 1000 ng/mL or (ii) about 50 mg, when the plasma concentration of the CSA is less than about 200 ng/mL.

In exemplary aspects, the method comprises administering to the subject an initial dose of OM twice a day during the initial time period of about 4 weeks, wherein each initial dose is about 25 mg administered via oral administration. In exemplary aspects, the method comprises a second time period which follows the initial time period, and, during the second time period, a second series of doses is administered to the subject based on the subject's plasma concentration of the CSA measured during the initial time period, e.g., at about 2 weeks from the time the first initial dose is administered. In exemplary instances, the method comprises a third time period which follows the second time period, and, during the second time period, a third series of doses is administered to the subject based on the subject's plasma concentration of the CSA measured during the second time period, e.g., at about 6 weeks from the time the first initial dose is administered. In exemplary aspects, each dose of the second and third series is administered twice daily via oral administration. In exemplary aspects, the therapeutic concentration range is about 200 ng/mL to about 1000 ng/mL and the following schematics are followed for the second and third series of doses:

|  | Subject's Plasma Concentration of CSA | Time at which Subject's Plasma Concentration Measured*** | Amount of each dose of Second Series |
|---|---|---|---|
| Second Series of Doses | ≥1000 ng/mL | 2 weeks | 0 mg |
|  | ≥300 to <1000 ng/mL | 2 weeks | 25 mg |
|  | ≥200 to <300 ng/mL | 2 weeks | 37.5 mg |
|  | <200 ng/mL | 2 weeks | 50 mg |
| Third Series of Doses | <750 ng/mL | 6 weeks | Same dose administered during Second Series |
|  | ≥750 to <1000 ng/mL | 6 weeks | 25 mg, if Dose during Second Series = 25 mg or 37.5 mg<br>37.5 mg, if dose during second series = 50 mg |
|  | ≥1000 ng/mL | 6 weeks | 25 mg if dose during second series is 37.5 mg or 50 mg<br>0 mg if dose during second series is 25 mg |

***Time after 1st initial dose administration

In exemplary aspects, the second time period is about 4 weeks and the third time period is at least about 4 weeks. In exemplary aspects, if the subject's plasma concentration of the CSA is greater than or about 1000 ng/mL, administrations of the CSA cease. In exemplary aspects, the plasma concentration of the CSA is measured or determined every 4, 6, 12, 24, or 48 weeks.

In exemplary embodiments, the method of treating a subject with heart failure (HF), comprises (a) administering to the subject a series of initial doses of omecamtiv mecarbil (OM) twice daily via oral administration for an initial time period of about 4 weeks, each initial dose of which is about 25 mg, and (b) administering to the subject a subsequent series of doses of OM twice daily via oral administration for a second time period that follows the initial time period, wherein each subsequent dose is (i) about 25 mg, when the subject's plasma concentration measured at about 2 weeks from the beginning of the initial time period is greater than or about 300 ng/mL, (ii) about 37.5 mg, when the subject's plasma concentration measured at about 2 weeks from the beginning of the initial time period is greater than or about 200 ng/mL but less than 300 ng/mL, or (iii) about 50 mg, when the subject's plasma concentration measured at about 2 weeks from the beginning of the initial time period is less than 200 ng/mL. In exemplary aspects, the method further comprises measuring the subject's plasma concentration at about 2 weeks from the beginning of the initial time period. In exemplary instances, the second time period is about 4 weeks following the initial time period. In some aspects, the method further comprises administering to the subject a subsequent series of doses of OM twice daily via oral administration for a third time period that follows the second time period, wherein each subsequent dose administered during the third time period is based on the subject's plasma concentration measured at about 6 weeks from the beginning of the initial time period. In exemplary aspects, (A) when the subject's plasma concentration measured at about 6 weeks from the beginning of the initial time period is less than 750 ng/mL, each dose of the third time period is about the same as the subsequent dose of the second time period; (B) when the subject's plasma concentration measured at about 6 weeks from the beginning of the initial time period is greater than or about 750 ng/mL and less than 1000 ng/mL and the subsequent dose administered during the second time period is 25 mg or 37.5 mg, each dose of the third time period is about 25 mg; (C) when the subject's plasma concentration measured at about 6 weeks from the beginning of the initial time period is greater than or about 750 ng/mL and less than 1000 ng/mL and the subsequent dose administered during the second time period is about 50 mg, each dose of the third time period is about 37.5 mg; (D) when the subject's plasma concentration measured at about 6 weeks from the beginning of the initial time period is greater than or about 1000 ng/mL and the subsequent dose administered during the second time period is about 25 mg, each dose of the third time period is about 0 mg; and (E) when the subject's plasma concentration measured at about 6 weeks from the beginning of the initial time period is greater than or about 1000 ng/mL and the subsequent dose administered during the second time period is about 37.5 mg or about 50 mg, each dose of the third time period is about 25 mg. In exemplary instances, the third time period is at least or about 4 weeks following the second time period. In exemplary aspects, the method further comprises measuring the subject's plasma concentration at about 6 weeks from the beginning of the initial time period.

Related Methods

The present disclosure provides methods of preventing a serious adverse event during treatment with a cardiac sarcomere activator (CSA) in a subject. In exemplary embodiments, the method comprises (a) administering to the subject an initial dose of a CSA for an initial time period and (b) subsequently administering to the subject a dose of the CSA based on the subject's plasma concentration of the CSA at the end of the initial time period. In exemplary aspects, the initial dose is the minimum effective dose (MED) of the CSA. In exemplary aspects, the CSA has reached steady state in the subject by the end of the initial time period or by the time the plasma concentration of the CSA is determined. In exemplary aspects, the dose that is subsequently administered to the subject is one of two options: the subsequently administered dose is either the same as the initial dose or is greater than the initial dose. In alternative or additional exemplary aspects, the dose that is subsequently administered to the subject is one of three options: the subsequently administered dose is (i) the same as the initial dose, (ii) greater than the initial dose but lower than a maximum dose, or (iii) a maximum dose. In exemplary aspects, when the subject's plasma concentration of the CSA is greater than a threshold concentration, the subsequently administered dose is the same as the initial dose. In exemplary instances, the threshold concentration is about 1.0 to about 1.5 times the minimum of a target concentration range. In exemplary aspects, when the subject's plasma concentration of the CSA is less than the threshold, the subsequently administered dose is greater than the initial dose. In exemplary instances, the threshold concentration is about 1.0 times to about 1.5 times the minimum of a target concentration range.

In exemplary embodiments, the method of preventing a serious adverse event during treatment with a cardiac sarcomere activator (CSA) in a subject, comprises (a) administering to the subject an initial dose of a CSA for an initial time period, and (b) subsequently administering to the subject a dose of the CSA based on the subject's plasma concentration of the CSA during or at the end of the initial time period. In exemplary aspects, when the subject's plasma concentration of the CSA is greater than or equal to the minimum of a target concentration range, the subsequently administered dose is the same as the initial dose. In exemplary aspects, when the subject's plasma concentration of the CSA is less than the minimum of the target concentration range, the subsequently administered dose is greater than the initial dose. In exemplary aspects, when the subject's plasma concentration is greater than or about 1.5 times the minimum of a target concentration range, the subsequently administered dose is the same as the initial dose. In exemplary aspects, when the subject's plasma concentration of the CSA is less than 1.5 times the minimum of the target concentration range but greater than or about the minimum of the target concentration range, the subsequently administered dose is the greater than the initial dose but less than a maximum dose. In exemplary aspects, when the subject's plasma concentration of the CSA is less than the minimum of the target concentration range, the subsequently administered dose is the maximum dose.

As used herein, the term "prevent" and words stemming therefrom encompasses reducing the occurrence or delaying the onset of the medical condition (e.g., serious adverse event) being prevented. In exemplary aspects, the method delays the onset of the serious adverse event by 1 day, 2 days, 4 days, 6 days, 8 days, 10 days, 15 days, 30 days, two months, 4 months, 6 months, 1 year, 2 years, 4 years, or more. As used herein, the term "prevent" and words stemming therefrom encompasses reducing the risk of the serious adverse event. In exemplary aspects, the method reduces the risk of the serious adverse event 2-fold, 5-fold, 10-fold, 20-fold, 50-fold, 100-fold, or more.

The present disclosure provides methods of reducing risk of a serious adverse event during treatment with a cardiac sarcomere activator (CSA) in a subject. In exemplary embodiments, the method comprises (a) administering to the subject an initial dose of a CSA for an initial time period and (b) subsequently administering to the subject a dose of the CSA based on the subject's plasma concentration of the CSA at the end of the initial time period. In exemplary aspects, the initial dose is the minimum effective dose (MED) of the CSA. In exemplary aspects, the CSA has reached steady state in the subject by the end of the initial time period or by the time the plasma concentration of the CSA is determined. In exemplary aspects, the dose that is subsequently administered to the subject is one of two options: the subsequently administered dose is either the same as the initial dose or is greater than the initial dose. In alternative or additional exemplary aspects, the dose that is subsequently administered to the subject is one of three options: the subsequently administered dose is (i) the same as the initial dose, (ii) greater than the initial dose but lower than a maximum dose, or (iii) a maximum dose. In exemplary aspects, when the subject's plasma concentration of the CSA is greater than a threshold concentration, the subsequently administered dose is the same as the initial dose. In exemplary instances, the threshold concentration is about 1.0 to about 1.5 times the minimum of a target concentration range. In exemplary aspects, when the subject's plasma concentration of the CSA is less than the threshold, the subsequently administered dose is greater than the initial dose. In exemplary instances, the threshold concentration is about 1.0 times to about 1.5 times the minimum of a target concentration range.

In exemplary embodiments, the method of reducing risk of a serious adverse event during treatment with a cardiac sarcomere activator (CSA) in a subject, comprises (a) administering to the subject an initial dose of a CSA for an initial time period, and (b) subsequently administering to the subject a dose of the CSA based on the subject's plasma concentration of the CSA during or at the end of the initial time period. In exemplary aspects, when the subject's plasma concentration of the CSA is greater than or equal to the minimum of a target concentration range, the subsequently administered dose is the same as the initial dose. In exemplary aspects, when the subject's plasma concentration of the CSA is less than the minimum of the target concentration range, the subsequently administered dose is greater than the initial dose. In exemplary aspects, when the subject's plasma concentration is greater than or about 1.5 times the minimum of a target concentration range, the subsequently administered dose is the same as the initial dose. In exemplary aspects, when the subject's plasma concentration of the CSA is less than 1.5 times the minimum of the target concentration range but greater than or about the minimum of the target concentration range, the subsequently administered dose is the greater than the initial dose but less than a maximum dose. In exemplary aspects, when the subject's plasma concentration of the CSA is less than the minimum of the target concentration range, the subsequently administered dose is the maximum dose.

As used herein, the term "reducing" words stemming therefrom may not be a 100% or complete reduction. Rather, there are varying degrees of reduction of which one of ordinary skill in the art recognizes as having a potential benefit or therapeutic effect. In this respect, the risk of a serious adverse event may be reduced to any amount or level. In exemplary embodiments, the reduction of risk provided by the methods of the present disclosure is at least or about a 10% reduction (e.g., at least or about a 20% reduction, at least or about a 30% reduction, at least or about a 40% reduction, at least or about a 50% reduction, at least or about a 60% reduction, at least or about a 70% reduction, at least or about a 80% reduction, at least or about a 90% reduction, at least or about a 95% reduction, at least or about a 98% reduction).

The present disclosure further provides method of identifying a subject at risk for a serious adverse event during treatment with a cardiac sarcomere activator (CSA). In exemplary embodiments, the method comprises (a) administering to the subject an initial dose of a CSA for an initial time period and (b) determining the subject's plasma concentration of the CSA during or at the end of the initial time period. In exemplary aspects, the initial dose is the minimum effective dose (MED) of the CSA. In exemplary aspects, the initial timer period is at least about 2 weeks. In exemplary aspects, the CSA has reached steady state in the subject by the end of the initial time period or by the time the plasma concentration of the CSA is determined. In exemplary aspects, the method comprises determining the subject's steady state plasma concentration of the CSA. In exemplary aspects, when the subject's plasma concentration of the CSA is greater than a threshold concentration, the subject is identified as a subject at risk for a serious adverse event during treatment with a CSA. In exemplary aspects, such subjects are given subsequent doses of the CSA, but each subsequent dose is the same as the initial dose. In exemplary instances, the threshold concentration is about 1.0 to about 1.5 times the minimum of a target concentration range. In exemplary aspects, the target concentration range is about 200 ng/mL to about 1200 ng/mL or about 200 ng/mL to about 1000 ng/mL.

With regard to the methods of the present disclosure, the serious adverse event is myocardial infarction or myocardial ischemia. In exemplary aspects, the serious event is non-ST-elevation myocardial infarction. In exemplary aspects, the serious adverse event is one or more of: feeling hot, palpitations, chest or throat tightness, dizziness, tachycardia, ECG ST-segment depression, and positive cardiac markers.

Methods of determining a treatment regimen for a subject are further provided. In exemplary embodiments, the method comprises (a) administering to the subject the minimum effective dose (MED) dose of the CSA for an initial time period, wherein the CSA has reached a steady state in the subject during or by the end of the initial time period, and (b) determining the subject's plasma concentration of the CSA at the end of the initial time period. In exemplary aspects, the treatment regimen following the initial time period comprises a dose of the CSA that is either the same as the initial dose or is greater than the initial dose. In exemplary aspects, when the subject's plasma concentration of the CSA is greater than a threshold concentration, which in exemplary instances is about 1.0 to about 1.5 times the minimum of a target concentration range, the treatment regimen following the initial time period comprises a dose of the CSA that is the same as the initial dose. In exemplary aspects, when the subject's plasma concentration of the CSA is less than the threshold, which in exemplary instances is about 1.0 to about 1.5 times the minimum of a target concentration range, the treatment regimen following the initial time period comprises a dose of the CSA that is greater than the initial dose. In alternative or additional exemplary aspects, the treatment regimen following the initial time period comprises a dose that is one of three options: the subsequently administered dose is (i) the same as the initial dose, (ii) greater than the initial dose but lower than a maximum dose, or (iii) a maximum dose. In exemplary aspects, the treatment regimen following the initial time period comprises a dose of the CSA that is (i) essentially the same as the initial dose, when the plasma concentration of the CSA is greater than or about 1.5 times the minimum of the target concentration, (ii) greater than the initial dose but lower than a maximum dose, when the subject's plasma concentration of the CSA is greater than or about the minimum of the target concentration range but below about 1.5 times the minimum of the target concentration range, or (iii) a maximum dose, when the plasma concentration of the CSA is below the minimum of the target concentration range.

Such methods of determining a treatment regimen allow for optimizing the efficacy of treatment with a CSA.

The following examples are given merely to illustrate the present disclosure and not in any way to limit its scope.

EXAMPLES

Example 1

This example describes a randomized, placebo-controlled, double-blind, parallel group, multicenter, CV outcomes study for oral OM in subjects with HFrEF, including subjects with ongoing or history of HF hospitalization.

Approximately 8000 eligible subjects are randomized in a 1:1 ratio to receive either OM or placebo. Randomization is stratified by randomization setting (currently hospitalized for HF or recently and not currently hospitalized for HF) and region (5 strata: US and Canada; Latin America; Western Europe, South Africa, and Australasia; Eastern Europe including Russia; Asia). Approximately 25% or more of the total planned enrollment is to include subjects who are hospitalized at randomization. Enrollment of subjects with atrial fibrillation is to be limited to 20% of each enrollment setting.

OM is presented as tablets. Tablets are packaged in 14-count blisters.

OM is administered orally BID in the morning and evening by the subjects and is taken under fasted or fed conditions. OM is swallowed whole (not chewed, crushed, or split) and taken with water. Each morning and evening administration is taken at approximately the same time of day. If OM is not taken or has not been taken within approximately 12±3 hours from the most recent previous dose, the dose should be missed and the next dose should be taken at the regular time.

Subjects randomized to OM initiate administration at 25 mg BID. At study visit Week 2, a predose blood sample is collected for all subjects. The results are blinded to investigators. For subjects randomized to OM, predose PK collected at Week 2 guides the dose adjustment. A new OM supply is provided to a subject when PK is assessed for the purpose of dose adjustment regardless of randomized treatment group and outcome of the PK assessment in order to maintain the blind.

Subjects randomized to placebo receive placebo throughout the study and are submitted to all protocol procedures in order to maintain the blindness of treatment group allocation and OM dose. Subjects continue to take OM through the morning of the end of study (EOS) Visit A direct relationship has been observed between the plasma concentrations of OM and increases in systolic ejection time, stroke volume, and left ventricular function (Cleland et al, 2011; Teerlink et al, 2011). Excessive exposure to OM may result in signs and symptoms of myocardial ischemia or infarction (eg, increases in heart rate, dizziness, dyspnea, hypotension, chest discomfort or pain, ST-segment depression/elevation on ECG, and/or elevations in troponin I or T). No antidote to OM currently exists. In the event of an overdose, health care providers should be especially vigilant for signs and symptom of myocardial ischemia. Standard medical therapies should be used to treat adverse signs or symptoms that do not promptly resolve with discontinuation of the OM.

All subjects are to have predose PK assessed at Week 2 in order to guide the dose adjustment for subjects randomized to OM. At Week 6, another predose PK is assessed to reflect the PK results of the previous adjustment. Pharmacokinetics are assessed on Week 24 and Week 48, and every 48 weeks throughout the study. Table 1 provides a summary of dose adjustment rules.

TABLE 1

| Study Visit | Week 2 Plasma Concentration (ng/mL) | Current Dose BID | New Dose BID |
|---|---|---|---|
| Week 4 | <200 | 25 mg | 50 mg |
|  | ≥200-<300 |  | 37.5 mg |
|  | ≥300-<1000 |  | No change |
|  | ≥1000 |  | placebo |

| Study Visit | Week 6 Plasma Concentration (ng/mL) | Current Dose BID | New Dose BID |
|---|---|---|---|
| Week 8 | <750 | Any | No change |
|  | ≥750-<1000 | 25 mg | No change |
|  |  | 37.5 mg | 25 mg |
|  |  | 50 mg | 37.5 mg |
|  | ≥1000 | 25 mg | Placebo |
|  |  | 37.5 mg | 25 mg |
|  |  | 50 mg |  |

| Study Visit | Week 6 Plasma Concentration (ng/mL) | Current Dose | Now Dose |
|---|---|---|---|
| Week 24 | ≥1000 | Any | Withdraw IP |
| Week 48 |  |  |  |
| Q 48 weeks |  |  |  |
| Unscheduled |  |  |  |

BID = twice a day;
IP = investigational product;
Q 48 = every 48

A new investigational product supply is provided to all subjects at the Week 4 and Week 8 study visits regardless of randomized treatment group and outcome of the PK assessment in order to maintain the blind. If the Week 2 PK value is not available in time for dose adjustment, subjects randomized to OM are to continue with the 25 mg BID dose assignment pending the Week 6 PK assessment. If the Week 6 PK value is not available in time for the dose adjustment, subjects randomized to OM are assigned to the lower dosage regimen (25 mg BID).

At Week 12, Week 48, and every 48 weeks, PK is assessed and are not part of the PK-based dose adjustment approach. Subjects with plasma concentration 1000 ng/mL at assessments after the Week 8 visit are requested to stop OM administration, regardless of signs or symptoms. An extra visit is scheduled and the subject's treatment assignment is unblinded.

Subjects randomized to placebo receive placebo throughout the study but undergo identical PK and resupply procedures.

If OM cannot be taken or has not been taken within approximately 12±3 hours from the most recent previous dose, the dose should be missed and the next dose should be taken at the regular time.

If a subject experiences clinical signs or symptoms consistent with acute myocardial ischemia or infarction, the subject should receive immediate medical attention according to the institution's usual SoC, and the OM administration should be withheld. Serial cardiac ischemic markers and ECGs should be analyzed locally. Results from local laboratory assessment of Troponins (I or T), CK-MB, and BNP or NT-proBNP should be recorded in the CRF. A central laboratory PK sample, Troponin I, CK-MB, and NT-proBNP should be collected in all subjects experiencing such events as close as possible to the event, and the last OM administration time recorded. The results of the PK assessment, when present, routinely remain blinded to the sponsor and investigators.

Restarting OM after a cardiac ischemic event may be considered after appropriate management of the case, and assessment of the likely cause of the event and the potential relatedness of the event to OM. The decision to reinitiate the subject after a cardiac ischemic event should be discussed and agreed upon. Subjects experiencing acute cardiac ischemic events suspected to be related to OM should not be rechallenged. When restarting, subjects initiate OM 25 mg BID or placebo BID, according to initial group allocation. A new predose PK assessment will be conducted after 2 weeks from OM reinitiation, and dose adjustment will occur at the next OM dispensation visit. The adjustment follows the same procedures as for study visit Week 4, limiting the maximum dose to what was assigned before the event.

The primary endpoint of the study is composite of time to CV death or first HF event, whichever occurs first. An HF event is defined as an urgent, unscheduled clinic/office/ED visit, or hospital admission, with a primary diagnosis of HF, where the patient exhibits new or worsening symptoms of HF on presentation, has objective evidence of new or worsening HF, and receives initiation or intensification of treatment specifically for HF (Hicks et al, 2015). Changes to oral diuretic therapy do not qualify as initiation or intensification of treatment.

The secondary endpoints of the study include (i) time to CV death, (ii) change in Kansas City Cardiomyopathy Questionnaire Total Symptom Score (KCCQ TSS) from baseline to Week 24, (iii) time to first heart failure hospitalization, and (iv) time to all-cause death.

Additional endpoints include safety endpoints and exploratory endpoints.

Example 2

This example demonstrates the Inclusion and Exclusion Criteria of the study described in Example 1.

The inclusion criteria is as follows:
1. Subject has provided informed consent
2. Male or female, ≥18 to ≤85 years of age at signing of informed consent
3. History of chronic HF (defined as requiring treatment for HF for a minimum of 30 days before randomization)
4. LVEF ≤35%, per subject's most recent medical record, not in the setting of acute decompensation
5. NYHA class II to IV at most recent screening assessment
6. Managed with HF SoC therapies consistent with regional clinical practice guidelines according to investigator judgment of subject's clinical status oral SoC therapies for chronic HF (eg, beta blockers, renin-angiotensin-aldosterone system inhibitors) should be present, if not contraindicated. Subjects enrolled during either HF hospitalization or early after HF hospitalization discharge can be reinitiating or titrating oral SoC chronic HF therapies at the same time of randomization with the goal of achieving optimized therapy on study.
7. Current hospitalization with primary reason of HF or prior HF hospitalization, or urgent HF admission to emergency department (ED) within 1 year prior to screening
8. B-type natriuretic peptide (BNP) level ≥125 pg/mL or an NT-proBNP level ≥400 pg/mL at most recent screening assessment (subjects receiving angiotensin receptor-neprilysin inhibitor [ARNi] must use NT-proBNP assessment; for subjects with atrial fibrillation, the cut off levels are: BNP ≥375 pg/mL or NT-proBNP ≥1200 pg/mL)

The exclusion criteria is as follows:
9. Currently receiving treatment in another investigational device or drug study, or <30 days since ending treatment on another investigational device or drug study (ies). Other investigational procedures while participating in this study are excluded.
10. Malignancy within 5 years prior to randomization with the following exceptions: localized basal or squamous cell carcinoma of the skin, cervical intraepithelial neoplasia, stage 1 prostate carcinoma, breast ductal carcinoma in situ.
11. Subject has known sensitivity to any of the products or components to be administered during dosing.
12. Subject not likely to be available to complete all protocol-required study visits or procedures, and/or to comply with all required study procedures to the best of the subject and investigator's knowledge.
13. Inability to swallow study medication tablet (eg, swallowing disorders, feeding tubes)
14. Receiving mechanical hemodynamic support (eg, intra-aortic balloon pump counterpulsation), or mechanical ventilation (including non-invasive mechanical ventilation, ie, bilevel positive airway pressure [BiPAP] or continuous positive airway pressure [CPAP] devices) ≤7 days prior to randomization.
15. Receiving IV inotropes (eg, dobutamine, milrinone, levosimendan) or IV vasopressors (eg, epinephrine, norepinephrine, dopamine, or vasopressin) ≤3 days prior to randomization.
16. Receiving IV diuretics or IV vasodilators, or supplemental oxygen therapy ≤12 hours prior to randomization
17. Acute coronary syndrome (ST-elevation myocardial infarction, non-ST-elevation myocardial infarction, unstable angina), stroke, or transient ischemic attack, major cardiac surgery, percutaneous coronary intervention, or valvuloplasty within the 3 months prior to randomization
18. Implantable cardioverter defibrillator or initiation of cardiac resynchronization therapy (CRT) (with/without implantable cardioverter defibrillator) within 30 days prior to randomization
19. Severe uncorrected valvular heart disease, or hypertrophic obstructive cardiomyopathy, active myocarditis, constrictive pericarditis, or clinically significant congenital heart disease
20. Untreated severe ventricular arrhythmia (eg, ventricular tachycardia or ventricular fibrillation)
21. Chronic antiarrhythmic therapy, with the exception of amiodarone. Note: for the purposes of this exclusion criterion, digoxin, calcium channel blocker, and beta-blocker therapy are not considered to be chronic antiarrhythmic therapies
22. Symptomatic bradycardia or second or third degree heart block without a pacemaker
23. Routinely scheduled outpatient intravenous infusions for HF (eg, inotropes, vasodilators [eg, nesiritide], diuretics) or routinely scheduled ultrafiltration
24. Systolic blood pressure >140 mmHg or <85 mmHg, or diastolic blood pressure >90 mmHg, or heart rate >110 beats per minute, or <50 beats per minute at screening
25. Estimated glomerular filtration rate (eGFR)<20 mL/min/1.73 m$^2$ or receiving dialysis at screening 26. Hepatic impairment defined by a total bilirubin (TBL) 2 times the upper limit of normal (ULN), or alanine aminotransferase (ALT) or aspartate aminotransferase (AST) 3 times ULN at screening
27. Previously received OM
28. Severe, concomitant non-CV disease that is expected to reduce life expectancy to <2 years
29. Recipient of any major organ transplant (eg, lung, liver, heart, bone marrow, renal)
30. Female subject of childbearing potential who is not willing to inform her partner of her participation in this clinical study and to use 2 acceptable methods of effective birth control or practice true sexual abstinence (the reliability of sexual abstinence must be evaluated by the investigator and be the preferred and usual lifestyle of the subject) during treatment with IP (OM or placebo) and for an additional 5 days after the last dose of IP. If the female subject or her sole male partner has had a surgical contraceptive method (bilateral tubal ligation/occlusion or vasectomy with medical assessment of surgical success), additional contraceptive methods are not required. Male subject with a female partner of childbearing potential and not willing to inform his partner of his participation in this clinical study.
    a) A female is considered of childbearing potential unless she has had a hysterectomy, bilateral oophorectomy, or bilateral salpingectomy or she is postmenopausal. Menopause is defined as 12 months of spontaneous and continuous amenorrhea in a female 55 years old; or no spontaneous menses for at least 2 years in a female <55 years old; or age <55 years and spontaneous menses within the past 1 year, but currently amenorrheic (eg, spontaneous or secondary to hysterectomy) and with follicle-stimulating hormone (FSH) levels >40 IU/L, or postmenopausal estradiol levels (<5 ng/dL), or according to the definition of "postmenopausal range" for the laboratory involved.
    b) Two acceptable methods of effective birth control include the following 2 options:
        use of hormonal and barrier combination birth control methods (intrauterine device and barrier method with spermicide, intrauterine device and hormonal birth control method, hormonal birth control method and barrier method with spermicide),
        2 barrier methods (each partner must use 1 barrier method except a female condom) with at least 1 of the barrier methods including spermicide (a male and female condom may not be used together due to the risk of tearing)
    c) Hormonal methods of birth control include oral, intravaginal, transdermal, injectable, or implantable. Barrier methods of birth control include diaphragm with spermicide, cervical cap with spermicide, male or female condom with spermicide, and contraceptive sponge with spermicide. If spermicide is not commercially available in the local country/region a barrier method without spermicide is acceptable.
    Note: If additional medications are given during treatment which may alter the contraceptive requirements (these additional medications may require an increase in the number of contraceptive methods and/or length of time that contraception is to be utilized after the last dose of protocol-required therapies) the investigator is to discuss these changes with the study subject.
31. Female subject is pregnant or breastfeeding or is planning to become pregnant or planning to breastfeed during treatment with IP (OM or placebo) or within 5 days after the end of treatment with IP.
32. Planned to be discharged from the hospital to long term care facility (eg, skilled nursing facility) or hospice.
33. History or evidence of any other clinically significant disorder (including cardiac arrhythmia), condition or disease (with the exception of those outlined above) that, in the opinion of the investigator or a physician, if consulted, would pose a risk to subject safety or interfere with the study evaluation, procedures, or completion.

Example 3

This example demonstrates a phase 2, pharmacokinetic, randomized, placebo-controlled trial called chronic oral study of myosin activation to increase contractility in heart failure (COSMIC-HF), which was published in Teerlink et al., The Lancet 388: 2895-2903 (2016), which is incorporated by reference in its entirety.

Impaired contractility is a feature of heart failure with reduced ejection fraction. In this clinical trial, the pharmacokinetics and effects on cardiac function and structure of the cardiac myosin activator, omecamtiv mecarbil, were assessed.

This phase 2, pharmacokinetic, randomized, placebo-controlled trial was designed to investigate whether pharmacokinetic-guided dose titration of oral omecamtiv mecarbil given for 20 weeks would yield well tolerated plasma drug concentrations associated with improved ventricular systolic function and favorable ventricular remodeling Methods:

In this randomized, double-blind study, done at 87 sites in 13 countries, patients with stable, symptomatic chronic heart failure and left ventricular ejection fraction 40% or lower were recruited. Patients were randomly assigned equally, via an interactive web response system, to receive 25 mg oral omecamtiv mecarbil twice daily (fixed-dose group), 25 mg twice daily titrated to 50 mg twice daily guided by pharmacokinetics (pharmacokinetic-titration group), or placebo for 20 weeks. The maximum concentration of omecamtiv mecarbil in plasma (primary endpoint) and changes in cardiac function and ventricular diameters were assessed. This trial is registered with ClinicalTrials.gov, number NCT01786512.

Study Design

COSMIC-HF was an international, multicentre, randomised, parallel-group, placebo-controlled, double-blind study done at 87 sites in 13 countries. All patients provided written informed consent.

Patients

Eligible patients were aged 18-85 years and had chronic heart failure (New York Heart Association class II or Ill) treated with stable, optimum pharmacological therapy for at least 4 weeks, N-terminal pro B-type natriuretic peptide (NT-proBNP) concentrations in plasma of at least 200 pg/mL (≥1200 pg/mL if the patient presented with atrial fibrillation, although the proportion of patients with atrial fibrillation was limited to around 20% of the study population), left ventricular ejection fraction 40% or lower, and an echocardiogram with acceptable image quality (determined centrally by the echocardiography core laboratory, Brigham and Women's Hospital, Boston, Mass., USA). Patients were excluded if acute myocardial infarction, unstable angina, or persistent angina at rest had been diagnosed within 30 days before randomisation or they were receiving chronic anti-arrhythmic therapy (except amiodarone) or had severe chronic kidney disease (estimated glomerular filtration rate <30 mL/min per 173 m² at screening).

Randomization and Masking

Randomization was based on a computer-generated schedule prepared before the start of the study and stratified by presence or absence of atrial fibrillation or flutter. Patients were assigned in a 1:1:1 ratio, with the next allocation being obtained via an interactive web response system, to receive 25 mg oral omecamtiv mecarbil twice daily (fixed-dose group), 25 mg oral omecamtiv mecarbil twice daily titrated up to 50 mg twice daily (pharmacokinetic-titration group), or oral placebo. All pills and packaging were identical. The packaging included box numbers that were reconciled by the distribution system to ensure that the correct dose was received by patients.

Procedures

Before randomization, patients entered a screening period of up to 30 days for assessment with 12-lead electrocardiograph and echocardiograph and laboratory testing of chemistry, haematology, NT-proBNP concentration, and cystatin C concentration. Those eligible at the end of screening were randomized.

All patients received study treatment or placebo for 20 weeks and were followed up at week 24 after randomization. Patients in the pharmacokinetic-titration group received 25 mg omecamtiv mecarbil twice daily for 2 weeks to reach a steady state. If the trough omecamtiv mecarbil concentration in plasma before the morning dose (predose concentration) at 2 weeks was less than 200 ng/mL, the dose was titrated up to 50 mg twice daily at week 8. If the predose concentration was 200 ng/mL or higher, patients continued taking 25 mg twice daily until the end of the study. To access the pharmacokinetics in this population more rigorously than permitted by just trough sampling, intensive pharmacokinetic sampling was done at the end of weeks 2 and 12, over a period of 8 h on each day.

Patients attended study clinics at weeks 2 and 8, after which visits were every 4 weeks until week 24. Transthoracic echocardiograms were done at baseline, week 12, and week 20 and analyzed centrally. Blood samples were obtained at specified visits for analysis in the central laboratory. Cardiac troponin I concentrations in plasma were measured at baseline and weeks 2, 8, 12, 16, 20, and 24 with Siemens ADVIA Centaur Ultra Troponin I assay (Siemens, Tarrytown, N.Y., USA).[9,10] Possible cardiac ischaemia or infarction was adjudicated by the study's clinical events committee if investigators reported events suggestive of myocardial ischemia or if a patient's troponin I concentration was greater than the 99th percentile upper reference limit of 0.04 ng/mL when the previous concentration had been undetectable or if the value had increased by more than 0.03 ng/mL compared with the previously detected value.

Outcomes

The primary endpoint was the maximum concentration of omecamtiv mecarbil at the week 2 and 12 visits and the predose concentration at the week 2, 8, 12, 16, and 20 visits. Secondary endpoints were changes from baseline in systolic ejection time, stroke volume, left ventricular end-systolic and end-diastolic diameters, heart rate, and concentration of NT-proBNP in plasma at week 20. Additional prespecified exploratory echocardiographic endpoints included left ventricular fractional shortening, end-systolic and end-diastolic volumes, and ejection fraction. The clinical events committee adjudicated whether admissions to hospital and deaths and all episodes of myocardial ischaemia or infarction reported by investigators or based on an increase of cardiac troponin I concentration in plasma met the criteria for study endpoints.

Statistical Analysis

The standard deviations (SDs) for maximum and minimum concentrations of omecamtiv mecarbil in plasma were assumed to be in the range of 40-140 ng/mL.[6-8,11-13] On this basis, it was calculated that 142 patients in the pharmacokinetic-titration group would provide a two-sided 95% CI with half width of 6.6-23.0 ng/mL, assuming that 5% of patients would not have assessable concentrations of omecamtiv mecarbil, which was deemed sufficient for accurate population estimates of these concentrations. Previous work in a similar population of patients had shown that plasma concentrations of omecamtiv mecarbil as low as 100-200 ng/mL had some effect on cardiac function, but that the effect on stroke volume seemed to plateau with concentrations greater than 400 ng/mL, and that plasma concentrations greater than 1200 ng/mL were not clinically tolerated.[7] Thus, it was attempted to achieve a maximum concentration greater than 200 ng/mL and avoid exposures to concentrations greater than 1000 ng/mL. Additionally, with 150 patients in each group and significance set at $\alpha=0.05$ (two-sided), it was estimated that the statistical power for detecting a treatment effect on the echocardiographic endpoints of systolic ejection time, stroke volume, and left ventricular end-systolic diameter would be more than 90%. Differences between groups for changes in echo cardio graphic variables, heart rate, and NT-proBNP con cen trations from baseline were estimated with a repeated measures model fitted separately for each variable and that included the stratification factors of presence or absence of atrial fibrillation or flutter at randomisation, baseline value, treatment group, visit, and treatment group by visit interaction. An unstructured covariance matrix was used to account for the correlation between visits within patients. Least squares mean differences with 95% Cls of the mean relative to placebo are presented unless otherwise indicated. As the study was hypothesis generating, all p values are nominal with no multiplicity adjustment. This study is registered with ClinicalTrials.gov, number NCT01786512.

Findings:

From Mar. 17, 2014, to Mar. 5, 2015, 150 patients in the fixed-dose omecamtiv mecarbil group and 149 in the pharmacokinetic-titration and placebo groups were enrolled. Mean maximum concentration of omecamtiv mecarbil at 12 weeks was 200 (SD 71) ng/mL in the fixed-dose group and 318 (129) ng/mL in the pharmacokinetic-titration group. For the pharmacokinetic-titration group versus placebo group at 20 weeks, least square mean differences were as follows: systolic ejection time 25 ms (95% CI 18-32, p<0.0001), stroke volume 3.6 mL (0.5-6.7, p=0.0217), left ventricular end-systolic diameter −1.8 mm (−2.9 to −0.6, p=0.0027), left ventricular end-diastolic diameter −1.3 mm, (−2.3 to 0.3, p=0.0128), heart rate −3.0 beats per min (−5.1 to −0.8, p=0.0070), and N-terminal pro B-type natriuretic peptide concentration in plasma −970 pg/mL (−1672 to −268, p=0.0069). The frequency of adverse clinical events did not differ between groups.

Figure 2:
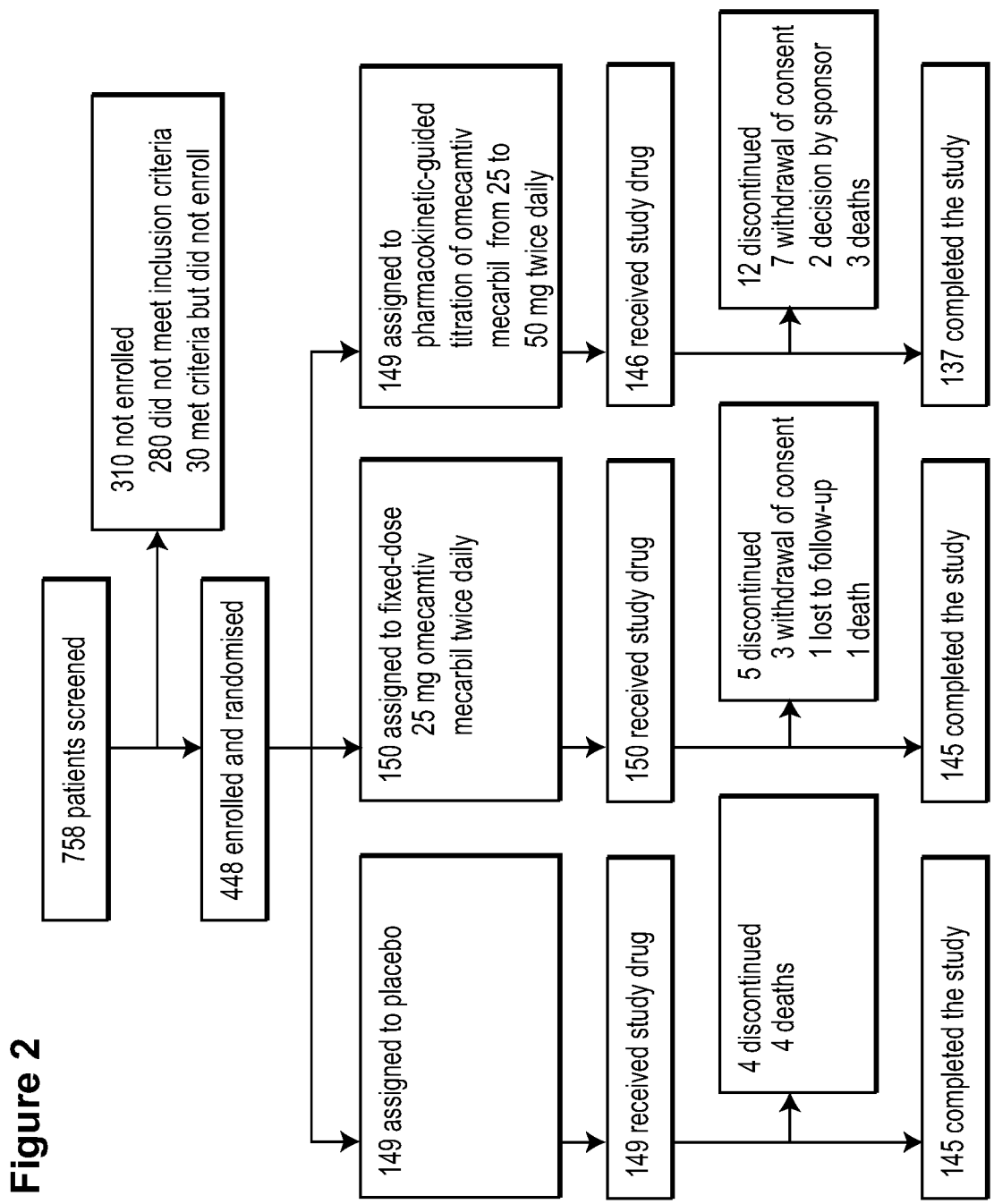
FIG. 2 is an illustration of the clinical trial profile described in Example 3.
Figure 3A:
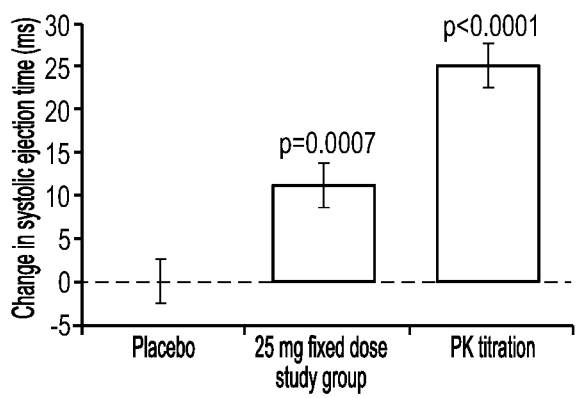
FIG. 3A is a graph of the change in systolic ejection time.
Figure 3B:
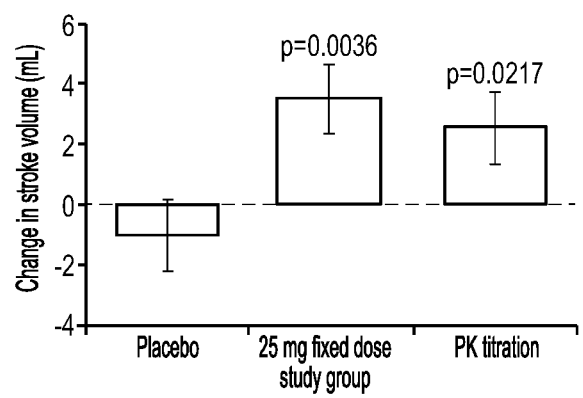
FIG. 3B is a graph of the change in stroke volume.
Figure 3C:
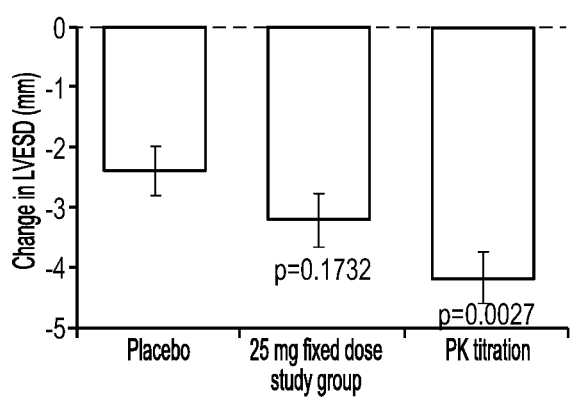
FIG. 3C is a graph of the change in LVESD.
Figure 3D:
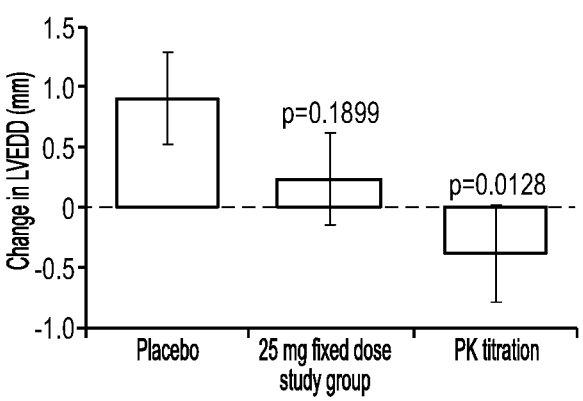
FIG. 3D is a graph of the change in LVEDD.
Figure 3E:
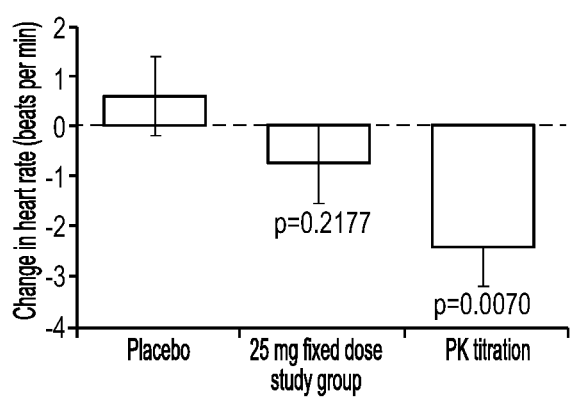
FIG. 3E is a graph of the change in heart rate.
Figure 3F:
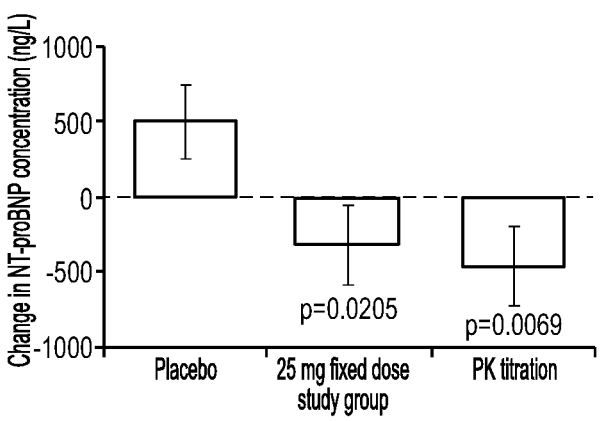
FIG. 3F is a graph of the change in NT-proBNP. The p values are for comparison with the placebo group. LVESD=left ventricular end systolic diameter; LVEDD=left ventricular end diastolic diameter; NT-proBNP=N-terminal brain natriuretic peptide; PK=pharmacokinetic.

Of 758 patients screened from Mar. 17, 2014, to Mar. 5, 2015, 448 were enrolled, of whom 149 were randomly assigned to the placebo group, 150 to the fixed-dose group, and 149 to the pharmacokinetic-titration group (FIG. 2). The groups were balanced for most baseline characteristics, and most patients were receiving recommended pharmacological therapy for chronic heart failure (table 2). 285 (64%) had implantable cardioverter defibrillators, cardiac resynchronisation pacemakers, or both.

TABLE 2

| Baseline Characteristics | | | |
|---|---|---|---|
| | Placebo group (n = 149) | Fixed-dose omecamtiv mecarbil group (n = 150) | Pharmacokinetic-titration omecamtiv mecarbil group (n = 149) |
| Age (years) | 64 (10) | 63 (10) | 63 (12) |
| Sex | | | |
| Men | 119 (80%) | 127 (85%) | 125 (84%) |
| Women | 30 (20%) | 23 (15%) | 24 (16%) |
| White ethnic origin (%) | 136 (91%) | 142 (95%) | 140 (94%) |
| BMI (kg/m2) | 29·7 (5·7) | 28·5 (5·6) | 29·5 (6·1) |
| Systolic blood pressure (mm Hg) | 119 (14) | 121 (16) | 119 (16) |
| Heart rate (beats per min) | 69 (10) | 67 (11) | 70 (12) |
| Heart failure characteristics | | | |
| Ischaemic heart disease | 89 (60%) | 97 (65%) | 101 (68%) |
| Time from heart failure diagnosis (years) | 8·0 (7·1) | 7·7 (7·9) | 7·7 (6·5) |
| Admitted to hospital for heart failure in previous 12 months | 38 (26%) | 51 (34%) | 38 (26%) |
| NYHA class | | | |
| II | 105 (70%) | 102 (68%) | 107 (72%) |
| III | 44 (30%) | 48 (32%) | 42 (28%) |
| Comorbidities | | | |
| Angina | 32 (21%) | 41 (27%) | 50 (34%) |
| History | | | |
| Myocardial infarction | 82 (55%) | 83 (55%) | 82 (55%) |
| Unstable angina | 20 (13%) | 28 (19%) | 27 (18%) |
| Coronary angiogram with clinically relevant stenosis | 70 (47%) | 73 (49%) | 78 (52%) |
| Percutaneous intervention | 62 (42%) | 61 (41%) | 63 (42%) |
| CABG* | 28 (19%) | 47 (31%) | 40 (27%) |
| Persistent atrial fibrillation or flutter | 33 (22%) | 28 (19%) | 24 (16%) |
| Diabetes mellitus | 61 (41%) | 70 (47%) | 55 (37%) |
| Hypertension | 101 (68%) | 94 (63%) | 109 (73%) |
| Dyslipidaemia | 111 (74%) | 95 (63%) | 99 (66%) |
| Transient ischaemic attack | 9 (6%) | 10 (7%) | 5 (3%) |
| Stroke | 14 (9%) | 15 (10%) | 14 (9%) |
| Chronic obstructive pulmonary disease | 23 (15%) | 21 (14%) | 15 (10%) |
| Laboratory variables† | | | |
| Median (IQR) cardiac troponin I (ng/mL) | 0·025 (0·016-0·041) | 0·022 (0·016-0·039) | 0·022 (0·016-0·042) |
| Median (IQR) NT-proBNP (pg/mL) | 1719 (699-3242%) | 1538 (634-3427%) | 1719 (881-3060%) |
| Estimated glomerular filtration rate (mL/min per 1·73 m2) | 65 (19) | 63 (19) | 65 (19) |
| Heart failure therapies† | | | |
| ACE inhibitor, ARBs, or both | 140 (94%) | 142 (95%) | 137 (92%) |
| ACE inhibitors | 106 (71%) | 104 (69%) | 97 (65%) |
| ARBs | 36 (24%) | 42 (28%) | 40 (27%) |
| β blockers | 146 (98%) | 146 (97%) | 144 (97%) |
| Mineralocorticoid-receptor antagonists | 88 (59%) | 87 (58%) | 94 (63%) |
| Diuretics other than mineralocorticoid receptor antagonists | 125 (84%) | 128 (85%) | 134 (90%) |
| Digitalis glycosides | 31 (21%) | 24 (16%) | 32 (22%) |
| ICD only | 52 (35%) | 58 (39%) | 60 (40%) |
| Cardiac 57andomized57zation therapy without ICD | 6 (4%) | 2 (1%) | 1 (1%) |
| Cardiac 57andomized57zation therapy with ICD | 30 (20%) | 39 (26%) | 37 (25%) |
| Echocardiographic variables† | | | |
| Systolic ejection time (ms) | 299 (37) | 305 (39) | 298 (33) |
| Stroke volume (mL) | 52·2 (14·9) | 54·1 (15·4) | 52·4 (14·9) |
| LVESD (mm) | 53·1 (9·6) | 52·4 (8·6) | 53·9 (9·1) |
| LVEDD (mm) | 61·9 (9·6) | 61·2 (8·3) | 62·8 (9·0) |
| Fractional shortening (%) | 18·9 (5·5) | 18·7 (5·5) | 18·4 (5·3) |

TABLE 2-continued

| Baseline Characteristics | | | |
|---|---|---|---|
| | Placebo group (n = 149) | Fixed-dose omecamtiv mecarbil group (n = 150) | Pharmacokinetic-titration omecamtiv mecarbil group (n = 149) |
| LVESV (mL) | 155 · 9 (89 · 0) | 144 · 2 (61 · 3) | 157 · 1 (77 · 7) |
| LVEDV (mL) | 215 · 7 (99 · 2) | 1999 · (69 · 1) | 215 · 9 (88 · 8) |
| Ejection fraction (%) | 29 · 3 (7 · 4) | 29 · 3 (7 · 5) | 29 · 0 (7 · 3) |

Data are mean (SD) or number (%) unless stated otherwise.
NYHA = New York Heart Association.
CABG = coronary artery bypass grafting.
NT-proBNP = N-terminal pro B-type natriuretic peptide.
ACE = angiotensin-converting enzyme.
ARBs = angiotensin-II-receptor blockers.
ICD = implantable cardioverter defibrillator.
LVESD = left ventricular end-systolic diameter.
LVEDD = left ventricular end-diastolic diameter.
LVESV = left ventricular end-systolic volume.
LVEDV = left ventricular end-diastolic volume.
*Difference between groups p<0.05.
†Excludes three patients who were 57andomized but did not receive study treatment or placebo.

At week 8, the dose of omecamtiv mecarbil was titrated up to 50 mg twice daily in 78 (53%) of 146 patients in the pharma cokinetic-titration group. At week 12, the mean omecamtiv mecarbil concentration was 165 (SD 68) ng/mL in the fixed-dose group and 263 (116) ng/mL in the pharmacokinetic-titration group, and the mean maximum concentrations were 200 (71) ng/mL and 318 (129) ng/mL, respectively (table 3). At week 12, 63 (46%) of 137 patients with measurements available in the fixed-dose group and 110 (87%) of 127 in the pharmacokinetic-titration group had maximum drug concentrations in plasma greater than or equal to 200 ng/mL. Maximum concentrations were less than 1000 ng/mL in all patients, and only one patient in the pharmacokinetic-titration group had a maximum concentration greater than 750 ng/mL. The maximum observed concentration of omecamtiv mecarbil in plasma at any time during the study was 453 ng/mL in the fixed-dose group and 831 ng/mL in the pharmacokinetic-titration group.

TABLE 3

| Concentrations of study drug in plasma | | |
|---|---|---|
| | Fixed Dose OM Group | Pharmacokinetic-titration OM Group |
| Predose Concentration (ng/mL) | | |
| Week 2 | 174 (62.2) 35.7% | 179 (68.8) 38.4% |
| Week 8 | 156 (69.1) 44.2% | 161 (74.4) 46.1% |
| Week 12 | 165 (67.9) 41.3% | 263 (116) 44.1% |
| Week 16 | 155 (69.0) 44.6% | 240 (120) 50.0% |
| Week 20 | 149 (71.2) 47.8% | 239 (118) 49.5% |
| Maximum Concentration (ng/mL) | | |
| Week 2 | 212 (70.4) 33.2% | 212 (81.0) 38.2% |
| Week 12 | 200 (71.1) 35.6% | 318 (129) 40.5% |

OM = omecamtiv mecarbil; Data are mean (SD) and coefficient of variation.
* includes five patients who discontinued study before day 50 and who were not treated after week 8.

All prespecified secondary efficacy endpoints in the pharmacokinetic-titration group differed significantly from those in the placebo group at week 20 (FIG. 3). Placebo-corrected increases at week 20 were seen in both omecamtiv mecarbil groups for systolic ejection (11 ms, 95% CI 5-18, p=0.0007 in the fixed-dose group and 25 ms, 18-32, p<0.0001 in the pharmacokinetic-titration group) and stroke volume (5 mL, 2-8, p=0.0036 and 4 mL, 1-7, p=0.0217, respectively). Left ventricular end-systolic and end-diastolic diameters and heart rate were reduced in the pharmacokinetic-titration omecamtiv mecarbil group compared with in the placebo group at week 20, but not in the fixed-dose group. Concentrations of NT-proBNP in plasma at 20 weeks, however, were reduced in both omecamtiv mecarbil groups (−822 pg/mL, 95% CI −1516 to −127, p=0.0205 in the fixed-dose group and −970 pg/mL, −1672 to −268, p=0.0069 in the pharmacokinetic-titration group), which persisted 4 weeks after omecamtiv mecarbil was stopped (−1327 pg/mL, −2056 to −597, p=0.0004 and −1306 pg/mL, −2046 to −566, p=0.0006, respectively). Additionally, in the pharma cokinetic-titration group, reductions in left ventricular end-diastolic and end-systolic volumes and increases in fractional shortening were seen at week 20 compared with placebo.

Figure 4:
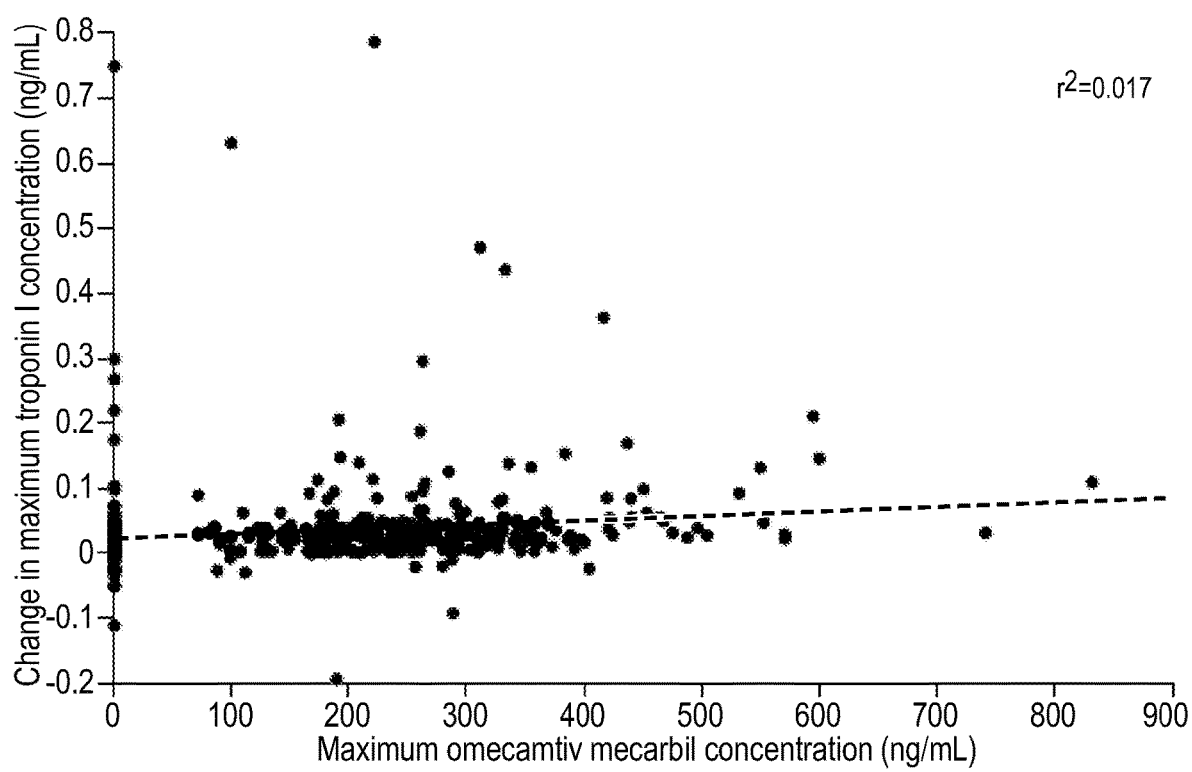
FIG. 4 is a graph depicting the change from baseline in maximum cardiac troponin I concentration in relation to maximum omecamtiv mecarbil concentration in plama. Each dot represents one patient (n=429). The linear regression line for change in maximum troponin I concentration, calculated as (0.000066×maximum omecamtiv mecarbil concentration)+0.023, shows a very poor correlation with maximum omecamtiv mecarbil plasma concentration ($r^2$=0.017).

Similar percentages of patients in the three groups completed the courses of the study drug and placebo (table 3). The frequencies of adverse events, serious adverse events, and deaths were similar across randomized groups. Around a quarter of enrolled patients had cardiac troponin I concentrations in plasma greater than the 99$^{th}$ percentile upper reference limit (0.04 ng/mL) at baseline, with proportions being similar across groups. At week 20, compared with placebo, concentrations of cardiac troponin I were increased in patients receiving fixed-dose and titrated omecamtiv mecarbil. The median changes from baseline were 0.001 ng/mL in the fixed-dose omecamtiv mecarbil group and 0.006 ng/mL with pharmacokinetic-titration group, whereas no change was seen in the placebo group (table 4). The maximum changes from baseline at any time during the 20 weeks of treatment achieved significance in the omecamtiv mecarbil groups compared with placebo (p=0.0029 in the fixed-dose group and p<0.0001 in the pharmacokinetic-titration group). Of these increases, 92% were less than 0.1 ng/mL, and 97% were less than 0.2 ng/mL in patients assigned to omecamtiv mecarbil, compared with 95% and 97%, respectively, in patients assigned to placebo. Plasma concentrations of cardiac troponin I returned to baseline levels within 4 weeks of discontinuing omecamtiv mecarbil. The maximum concentration of omecamtiv mecarbil was poorly predictive of the maximum change from baseline in cardiac troponin I concentration (FIG. 4). 278 potential adverse events triggered increases in cardiac troponin I concentrations were submitted to the clinical events committee for adjudication. Of these, none was deemed to be an episode of myocardial ischaemia or a myocardial infarction. sodes of tachycardia, hypotension, atrial or ventricular arrhythmia, cardiac ischaemia, or myocardial infarction were seen with the oral drug. The incidence of clinical

TABLE 4

Safety variables and adverse events

|  | Placebo (n = 149) | Fixed-dose OM group (n = 150) | Pharmacokinetic-titration OM group (n = 146) |
|---|---|---|---|
| Tolerability | | | |
| Completed treatment | 133 (89%) | 134 (89%) | 127 (85%) |
| Discontinued treatment | 16 (11%) | 16 (11%) | 19 (13%) |
| Cardiac troponin I concentrations (ng/mL) | | | |
| Change to Week 20 | 0 (−0.007 to 0.004) | 0.001 (0 to 0.012) | 0.006 (0 to 0.024) |
| Maximum change from baseline | 0.01 (0 to 0.020) | 0.016 (0.003 to 0.034) | 0.020 (0.005 to 0.038) |
| Change to Week 24 | 0 (−0.006 to 0.008) | 0 (−0.002 to 0.009) | 0 (−0.003 to 0.010) |
| Adjudicated clinical events | | | |
| Hospital admission | 24 (16%) | 24 (16%) | 26 (18%) |
| Heart Failure | 11 (7%) | 9 (6%) | 10 (7%) |
| Myocardial infarction | 1 (1%) | 0 | 1 (1%) |
| Unstable angina | 0 | 1 (1%) | 0 |
| Chest paint | 1 (1%) | 2 (1%) | 2 (1%) |
| Other categories | 15 (10%) | 14 (9%) | 15 (10%) |
| Total myocardial infarction** | 2 (1%) | 0 | 1 (1%) |
| Death | 4 (3%) | 1 (1%) | 3 (2%) |
| Cardiovascular death | 2 (1%) | 1 (1%) | 2 (1%) |
| Adverse events | | | |
| Any | 91 (61%) | 92 (61%) | 95 (65%) |
| Most frequent§ | | | |
| Dyspnoea | 8 (5%) | 11 (7%) | 13 (9%) |
| Fatigue | 4 (3%) | 14 (9%) | 9 (6%) |
| Dizziness | 6 (4%) | 8 (5%) | 10 (7%) |
| Cardiac failure | 13 (9%) | 5 (3%) | 8 (5%) |
| Nasopharyngitis | 5 (3%) | 8 (5%) | 5 (3%) |
| Leading to study discontinuation | 12 (8%) | 8 (5%) | 12 (8%) |
| Serious adverse events | 30 (20%) | 36 (24%) | 32 (22%) |
| Cardiac | 19 (13%) | 18 (12%) | 17 (12%) |
| Cardiac failure | 4 (3%) | 3 (2%) | 5 (3%) |
| Acute cardiac failure | 1 (1%) | 3 (2%) | 3 (2%) |
| Congestive cardiac failure | 3 (2%) | 3 (2%) | 3 (2%) |
| Angina pectoris | 0 | 3 (2%) | 1 (1%) |
| Ventricular tachycardia | 1 (1%) | 2 (1%) | 1 (1%) |

Data are number (%) or median (IQR).
*Includes three patients who were randomised but did not receive study drug.
†Excludes myocardial infarction and unstable angina.
‡None of 278 possible cardiac ischaemia or infarction events associated with increased cardiac troponin I concentrations and adjudicated by the clinical events committee were deemed to be myocardial infarction.
§Judged to be related to treatment and occurring in ≥5% of patients.

In COSMIC-HF, target plasma drug concentrations could be achieved with oral administration of omecamtiv mecarbil in patients with chronic heart failure and reduced ejection fraction, although almost twice as many patients in the pharmacokinetic-titration group than in the fixed-dose group attained target concentrations. Patients in the pharmacokinetic-titration group had increased duration of ventricular systolic ejection time and stroke volume and reduced left ventricular diameters and volumes, NT-proBNP plasma concentrations, and heart rate compared with placebo. These effects on cardiac function were similar to those seen in earlier preclinicar and clinical studies[6-8] of short-term intravenous omecamtiv mecarbil. No increases in clinical epi- adverse events in this study was similar with placebo and omecamtiv mecarbil, although the safety assessment was limited by the small sample size, and patients receiving omecamtiv mecarbil had small increases in plasma concentrations of cardiac troponin I, but these returned to baseline values after treatment was discontinued. Our findings support the hypothesis that direct and selective augmentation of systolic function can reduce stress on the myocardial wall (as suggested by the decrease in NT-proBNP concentrations in plasma) and possibly sympathetic activation (as suggested by the decrease in heart rate), and might promote favourable ventricular remodelling in patients with chronic heart failure and reduced ejection fraction.

Omecamtiv mecarbil is a selective cardiac myosin activator that binds to the motor domain of myosin and increases its probability of engaging the actin filament productively to produce force during systole.[4] This mechanism of action directly improves cardiac contractility by specifically modulating the function of the sarcomere. In preclinical studies, omecamtiv mecarbil did not increase the calcium transient in cardiac myocytes, and has no known activity other than its action on cardiac myosin that could account for its effects on cardiovascular function. In animals[4,5] and human beings,[6-8] the pharmacodynamic signature of omecamtiv mecarbil is an increase in the systolic ejection time. This finding is a reflection of the drug's mechanism of action, that is, the increase in the number of myosin heads interacting with actin filaments facilitates a longer duration of systole, even as cytoplasmic calcium concentrations fall in the myocyte.

Systolic ejection times in patients with systolic heart failure are shortened by 10-70 ms compared with those in healthy controls.[14] The exact mechanism underlying this decrease in systolic ejection time is unknown, although the effect is proportional to the decrease in stroke volume. In an analysis of 2077 patients from the ARIC study,[15] decreased systolic ejection time was directly related to decreased fractional shortening and predicted the future risk of heart failure. Consistent with studies of intravenous administration in healthy volunteers and patients with acute and chronic heart failure,[6-8] chronic oral administration of omecamtiv mecarbil in this study was associated with extended systolic ejection times, with average increases of 11-25 ms, bringing the systolic ejection times closer to normal.

In a contemporary model of the pathogenesis of heart failure, decreased systolic function leads to multiple pathophysiological adaptations, including activation of the rening-angiotensing-aldosterone system (RAAS) and sympathetic system and adverse ventricular remodelling, which result in worsening cardiac function and symptoms. This hypothesis has been supported by trials in which blocking of the RAAS and sympathetic system (eg, with angiotensin-converting-enzyme inhibitors, angiotensin-II-receptor blockers, mineralo corticoid-receptor antagonists, and 13 blockers) or augmentation of vasodilating peptides (eg with neprilysin inhibitors) have slowed or prevented the progression of heart failure. So far, however, no pharmacological therapy has been available to test the hypothesis that direct and selective augmentation of cardiac function can also delay progression of heart failure. Although our study was not designed to test this hypothesis specifically, 20 weeks of omecamtiv mecarbil administration was associated with reduced left ventricular end-diastolic diameters and volumes. The ventricular diameters were not reassessed after omecamtiv mecarbil was stopped, but decreases in plasma concentrations of NT-proBNP persisted, which suggests that the effects on cardiac dimensions do not merely reflect a direct short-term effect on systolic function. The decreased heart rate associated with omecamtiv mecarbil in this study and earlier preclinicar and clinical studies[6-8] is also consistent with reduced sympathetic activation. Together, therefore, these findings from COSMIC-HF seem to support the hypothesis that directly improving systolic function can reverse maladaptive structural changes associated with the progression of heart failure.

In several previous studies, therapies that have improved ventricular remodeling have also had beneficial effects on clinical outcomes. In a meta-analysis of the relation between drug-related or device-related changes in ventricular volumes and mortality,[16] therapies that decreased end-diastolic or end-systolic volumes by a mean of 11 mL were associated with 65-75% likelihood of favourable effects on mortality. In the MADIT-CRT trial,[17] a 5% decrease in ventricular volume was associated with 14-20% reductions in the combined endpoint of death or admission to hospital for heart failure. Plasma concentrations of natriuretic peptides have also been strong predictors of adverse clinical outcomes, including cardiovascular death,[18,19] and in some studies have been stronger predictors of clinical outcomes than left ventricular ejection fraction or volume.[20] Similar changes after treatment with omecamtiv mecarbil were noted, and believe these findings warrant further investigation of this drug's effects on cardiovascular outcomes.

COSMIC-HF compared the ability of two dosing strategies to yield well tolerated plasma concentrations. With pharmacokinetic titration, the target plasma concentration of more than 200 ng/mL was achieved in 110 (87%) of 127 patients, compared with in 63 (46%) of 137 patients who received fixed-dose omecamtiv mecarbil. Importantly, no patients in either group had plasma concentrations greater than 1000 ng/mL. However, a small, potentially concerning, increase in cardiac troponin I concentrations in plasma was seen in recipients of omecamtiv mecarbil that resolved after treatment was stopped. These increases were not correlated with the maximum omecamtiv mecarbil plasma concentrations, as was shown in a previous study of patients with acute heart failure.[8] The magnitude of troponin release is similar to that in healthy endurance athletes[21] and within the limits of diurnal variation for patients without heart failure.[22] None of the increases in cardiac troponin I concentration was deemed to indicate myocardial ischaemia and all occurred in the context of improving systolic function, decreasing ventricular volumes, and declining NT-proBNP concentrations in plasma. Whether the raised troponin I concentrations are related to myocardial damage or other mechanisms (eg, exosomal trafficking[23]) is unknown, and the effects of omecamtiv mecarbil on clinical events will need to be addressed in a large outcomes trial.

COSMIC-HF was a phase 2, pharmacokinetic study without formal hypothesis testing and, consequently, the echocardiographic findings should be viewed as hypothesis generating. The study was prospectively powered to assess the secondary efficacy endpoints of systolic ejection time, stroke volume, and left ventricular end-systolic diameter. All findings in the pharmacokinetic-titration omecamtiv mecarbil group for all prespecified secondary efficacy endpoints were significantly different from those in the placebo group, but no adjustments for multiple comparisons were made. With these caveats, our findings support the hypothesis that directly and specifically improving cardiac systolic function with a cardiac myosin activator results in favourable ventricular remodelling. The effects on long-term morbidity and mortality remain untested, and the risks and benefits of omecamtiv mecarbil will only be possible to assess in a large outcomes trial.

This example demonstrated that omecamtiv mecarbil dosing guided by pharmacokinetics achieved plasma concentrations associated with improved cardiac function and decreased ventricular diameter.

REFERENCES

The following references are cited throughout the present disclosure:

Ambrosy A P, Fonarow G C, Butler J, et al. The global health and economic burden of hospitalizations for heart failure. *J Am Coll Cardiol.* 2014; 63(12):1123-1133.

Bhatia R S, Tu J V, Lee D S, et al. Outcome of heart failure with preserved ejection fraction in a population-based study. *N Engl J Med.* 2006; 355(3):260-269.

Bretz F, Maurer W, Brannath W, Posch M. A graphical approach to sequentially rejective multiple test procedures. *Statistics in Medicine.* 2009; 28:586-604.

Cleland J G, Teerlink J R, Senior R, et al. The effects of the cardiac myosin activator, omecamtiv mecarbil, on cardiac function in systolic heart failure: a double-blind, placebo controlled, crossover, dose-ranging phase 2 trial. *Lancet.* 2011; 378:676-683.

Dickstein K, Cohen-Solal A, Filippatos G, McMurray J J, Ponikowski P, Poole-Wilson P A, Stromberg A, van Veldhuisen D J, Atar D, Hoes A W, Keren A, Mebazaa A, Nieminen M, Priori S G, Swedberg K; ESC Committee for Practice Guidelines (CPG). ESC Guidelines for the diagnosis and treatment of acute and chronic heart failure 2008: the Task Force for the Diagnosis and Treatment of Acute and Chronic Heart Failure 2008 of the European Society of Cardiology. Developed in collaboration with the Heart Failure Association of the ESC (HFA) and endorsed by the European Society of Intensive Care Medicine (ESICM). *Eur Heart J.* 2008 October; 29(19): 2388-442.

Hampton J R, van Veldhuisen D J, Kleber F X, Cowley A J, Ardia A, Block P, Cortina A, Cserhalmi L, Follath F, Jensen G, Kayanakis J, Lie K I, Mancia G, Skene A M. Randomized study of effect of ibopamine on survival in patients with advanced severe heart failure. Second Prospective Randomised Study of Ibopamine on Mortality and Efficacy (PRIME II) Investigators. *Lancet.* 1997 April; 5(349): 971-7.

Go A S, Mozaffarian D, Roger V L, Benjamin E J, Berry J D, et al. Heart disease and stroke statistics-2013 update: a report from the American Heart Association. *Circulation.* 2013; 127:e6-e245.

Greene S J, Fonarow G C, Vaduganathan M, Khan S S, Butler J, Gheorghiade M. The vulnerable phase after hospitalization for heart failure. *Nat Rev Cardiol.* 2015 April; 12(4):220-9.

Haybittle J L. Repeated assessment of results in clinical trials of cancer treatment. *Br J Radiol.* 1971; 44(526): 793-797.

Hicks K A, et al. 2014 ACC/AHA Key Data Elements and Definitions for Cardiovascular Endpoint Events in Clinical Trials: A Report of the American College of Cardiology/American Heart Association Task Force on Clinical Data Standards. *J Am Coll Cardiol.* 2015; 28; 66:403-69.

Hilfiker-Kleiner D, Landmesser U, Drexler H. Molecular mechanisms in heart failure. Focus on cardiac hypertrophy, inflammation, angiogenesis, and apotosis. *J Am Coll Cardiol.* 2006; 48(9) (Suppl A:A56-66).

Jencks S F, Williams M V, Coleman E A N. Rehospitalizations among patients in the Medicare fee-for-service program. *Engl J Med.* 2009 Apr. 2; 360(14):1418-28.

Jessup M, Brozena S. Heart Failure. *N Engl J Med.* 2003; 348:2007-18.

Kannankeril P J, Pahl E, Wax D F. Usefulness of troponin I as a marker of myocardial injury after pediatric cardiac catheterization. *Am J Cardiol.* 2002 Nov. 15; 90(10): 1128-32.

Krum H, Teerlink J R. Medical therapy for chronic heart failure. Lancet. 2011; 378(9792):713-21.

Levy W C, Mozaffarian D, Linker D T, Sutradhar S C, Anker S D, et al. The Seattle Heart Failure Model: prediction of survival in heart failure. Circulation. 2006; 113(11):1424-33.

López-Sendón J. The heart failure epidemic. Medicographia. 2011; 33(4):363-369.

Malik F I, Hartman J J, Elias K A, et al. Cardiac myosin activation: a potential therapeutic approach for systolic heart failure. Science. 2011; 331:1439-1443.

McIlvennan C K, Allen L A. Outcomes in acute heart failure: 30-day readmission versus death. Curr Heart Fail Rep. 2014 December; 11(4):445-52.

Mozaffarian D, Anker S, Anand I, et al. Prediction of mode of death in heart failure: the Seattle heart failure model. Circulation. 2007; 116:392-398.

Omecamtiv mecarbil Investigator's Brochure. Thousand Oaks, Calif. Amgen Inc.

Packer M, Carver J R, Rodeheffer R R, et al. Effect of oral milrinone on mortality in severe chronic heart failure. The PROMISE Study Research Group. N Engl J Med. 1991 Nov. 21; 325 (21): 1468-75.

Peto R, Pike M C, Armitage P, Breslow N E, Cox D R, Howard S V, Mantel N, McPherson K, Peto J, Smith P G. Design and analysis of randomized clinical trials requiring prolonged observation of each patient. I. Introduction and design. Br J Cancer. 1976; 34(6):585-612.

Ponikowski P, Voors A A, Anker S D, et al. 2016 ESC Guidelines for the diagnosis and treatment of acute and chronic heart failure. Eur Heart J. 2016 August; 18(8): 891-975.

Shen Y T, Malik F I, Zhao X, et al. Improvement of cardiac function by a cardiac Myosin activator in conscious dogs with systolic heart failure. Circ. Heart Fail. 2010; 3:522-527.

Shih J H. Sample size calculation for complex clinical trials with survival endpoints. Control Clin Trials. 1995 December; 16(6):395-407.

Solomon S D, Wang D, Finn P, et al. Effect of candesartan on cause-specific mortality in heart failure patients the candesartan in heart failure assessment of reduction in mortality and morbidity (CHARM) program. Circulation. 2004; 110:2180-2183.

Tacon C L, McCaffrey J, Delaney A. Dobutamine for patients with severe heart failure: a systematic review and meta-analysis of randomised controlled trials. Intensive Care Med. 2012 March; 38(3):359-67.

Teerlink J R, Clarke C P, Saikali K G, et al. Dose-dependent augmentation of cardiac systolic function with the selective cardiac myosin activator, omecamtiv mecarbil: a first in-man study. Lancet. 2011; 378:667-675.

Yancy C, Jessup M, Bozkurt B et al. 2016 ACC/AHA/HFSA Focused Update on New Pharmacological Therapy for Heart Failure: An Update of the 2013 ACCF/AHA Guideline for the Management of Heart Failure. Circulation. 20 May 2016. Epub ahead of print. PMID 27208050. doi: 10.1161/CIR.0000000000000435.

Yancy C, Jessup M, Bozkurt B, Butler J, Casey D, et al. 2013 ACCF/AHA guideline for the management of heart failure: A report on the American College of Cardiology Foundation/American Heart Association Task Force on practice guidelines. *Circulation.* 2013; 128:e240-e327

The following references are cited throughout Example 3.

1 Braunwald E, Ross J Jr, Sonnenblick E H. Mechanisms of contraction of the normal and failing heart. *N Engl J Med* 1967; 277: 1012-22.

2 Packer M. The search for the ideal positive inotropic agent. *N Engl J Med* 1993; 329: 201-02.

3 Hasenfuss G, Teerlink J R. Cardiac inotropes: current agents and future directions. *Eur Heart J* 2011; 32: 1838-45.

4 Malik F I, Hartman J J, Elias K A, et al. Cardiac myosin activation: a potential therapeutic approach for systolic heart failure. *Science* 2011; 331: 1439-43.

5 Shen Y T, Malik F I, Zhao X, et al. Improvement of cardiac function by a cardiac myosin activator in conscious dogs with systolic heart failure. *Circ Heart Fail* 2010; 3: 522-27.

6 Teerlink J R, Clarke C P, Saikali K G, et al. Dose-dependent augmentation of cardiac systolic function with the selective cardiac myosin activator, omecamtiv mecarbil: a first-in-man study. *Lancet* 2011; 378: 667-75.

7 Cleland J G, Teerlink J R, Senior R, et al. The effects of the cardiac myosin activator, omecamtiv mecarbil, on cardiac function in systolic heart failure: a double-blind, placebo-controlled, crossover, dose-ranging phase 2 trial. *Lancet* 2011; 378: 676-83.

8 Teerlink J R, Felker G M, McMurray J J V, et al. Acute treatment with omecamtiv mecarbil to increase contractility in acute heart failure: the ATOMIC AHF study. *J Am Coll Cardiol* 2016; 67: 1444-55.

9 Apple F S. A new season for cardiac troponin assays: it's time to keep a scorecard. *Clin Chem* 2009; 55:1303-06.

10 Thygesen K, Alpert J S, Jaffe A S, et al. Third universal definition of myocardial infarction. *J Am Coll Cardiol* 2012; 60: 1581-98.

11 Palaparthy R, Banfield C, Alvarez P, et al. Relative bioavailability, food effect, and safety of the single-dose pharmacokinetics of omecamtiv mecarbil following administration of different modified-release formulations in healthy subjects. *Int J Clin Pharmacol Ther* 2016; 54: 217-27.

12 Vu T, Ma P, Xiao J J, Wang Y M, Malik F I, Chow A T. Population pharmacokinetic-pharmacodynamic modeling of omecamtiv mecarbil, a cardiac myosin activator, in healthy volunteers and patients with stable heart failure. J Clin Pharmacol 2015; 55: 1236-47.

13 Greenberg B H, Chou W, Saikali K G, et al. Safety and tolerability of omecamtiv mecarbil during exercise in patients with ischemic cardiomyopathy and angina. JACC Heart Fail 2015; 3: 22-29.

14 Weissler A M, Harris W S, Schoenfeld C D. Systolic time intervals in heart failure in man. Circulation 1968; 37: 149-59.

15 Biering-Sorensen T, Roca G Q, et al. Systolic ejection time is an independent predictor of incident heart failure in a community based cohort free of heart failure. J Card Fail 2015; 21: S84.

16 Kramer D G, Trikalinos T A, Kent D M, Antonopoulos G V, Konstam M A, Udelson J E. Quantitative evaluation of drug or device effects on ventricular remodeling as predictors of therapeutic effects on mortality in patients with heart failure and reduced ejection fraction: a meta-analytic approach. JAm Coll Cardiol 2010; 56: 392-406.

17 Solomon S D, Foster E, Bourgoun M, et al. Effect of cardiac resynchronization therapy on reverse remodeling and relation to outcome: multicenter automatic defibrillator implantation trial: cardiac resynchronization therapy. Circulation 2010; 122: 985-92.

18 Cleland J G, McMurray J J, Kjekshus J, et al. Plasma concentration of amino-terminal pro-brain natriuretic peptide in chronic heart failure: prediction of cardiovascular events and interaction with the effects of rosuvastatin: a report from CORONA (Controlled Rosuvastatin Multinational Trial in Heart Failure). J Am Coll Cardiol 2009; 54: 1850-59.

19 Rahimi K, Bennett D, Conrad N, et al. Risk prediction in patients with heart failure: a systematic review and analysis. JACC Heart Fail 2014; 2: 440-46.

20 Cleland J, Freemantle N, Ghio S, et al. Predicting the long-term effects of cardiac resynchronization therapy on mortality from baseline variables and the early response a report from the CARE-HF (Cardiac Resynchronization in Heart Failure) Trial. J Am Coll Cardiol 2008; 52: 438-45.

21 Shave R, Baggish A, George K, et al. Exercise-induced cardiac troponin elevation: evidence, mechanisms, and implications. J Am Coll Cardiol 2010; 56: 169-76.

22 Klinkenberg L J, van Dijk J W, Tan F E, van Loon L J, van Dieijen-Visser M P, Meex S J. Circulating cardiac troponin T exhibits a diurnal rhythm. J Am Coll Cardiol 2014; 63: 1788-95.

23 Waldenstrom A, Ronquist G. Role of exosomes in myocardial remodeling. Circ Res 2014; 114: 315-24.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method of treating a subject with heart failure (HF), comprising:
   a. administering to the subject an initial dose of a cardiac sarcomere activator (CSA) of 25 mg twice daily for an initial time period, b. subsequently administering to the subject a dose of the CSA based on the subject's plasma concentration of the CSA measured at about 2 weeks after the first administration of the initial dose, wherein the dose of the CSA is (i) about 25 mg twice daily when the subject's plasma concentration of the CSA is greater than or about 300 ng/mL, (ii) about 37.5 mg twice daily when the subject's plasma concentration of the CSA is greater than or about 200 ng/mL but less than 300 ng/mL, or (iii) about 50 mg twice daily, when the subject's plasma concentration of the CSA is less than 200 ng/mL; and wherein the CSA is omecamtiv mecarbil or a pharmaceutically acceptable salt thereof.

2. The method of claim 1, wherein the CSA has reached steady state in the subject by the end of the initial time period.

3. The method of claim 1, wherein the initial time period is about 1 to 3 weeks.

4. The method of claim 1, wherein the subject has chronic heart failure, or a New York Heart Association Class II or III heart failure.

5. The method of claim 1, wherein the OM is omecamtiv mecarbil dihydrochloride hydrate.

6. A method of treating a subject with heart failure (HF), comprising (a) administering to the subject a series of initial doses of omecamtiv mecarbil (OM) or a pharmaceutically acceptable salt thereof twice daily via oral administration for an initial time period of about 4 weeks, each initial dose of which is about 25 mg, and (b) administering to the subject a subsequent series of doses of OM twice daily via oral administration for a second time period that follows the initial time period, wherein each subsequent dose is (i) about 25 mg, when the subject's plasma concentration measured at about 2 weeks from the beginning of the initial time period is greater than or about 300 ng/mL, (ii) about 37.5 mg, when the subject's plasma concentration measured at about 2 weeks from the beginning of the initial time period is greater than or about 200 ng/mL but less than 300 ng/mL, or (iii) about 50 mg, when the subject's plasma concentration measured at about 2 weeks from the beginning of the initial time period is less than 200 ng/mL.

7. The method of claim 1, wherein the initial time period is at least or about 2 weeks.

8. The method of claim 1, wherein the subject has a left ventricular ejection fraction of about 40% or lower.

9. The method of claim 1, wherein the subject has a plasma concentration of NT-proBNP of at least about 200 pg/mL.

10. The method of claim 1, wherein the initial dose of OM or a pharmaceutically acceptable salt thereof is orally administered to the subject.

11. The method of claim 1, wherein the dose that is subsequently administered is about 50 mg.

12. The method of claim 1, wherein the dose that is subsequently administered is about 25 mg.

13. The method of claim 1, wherein the dose that is subsequently administered is about 37.5 mg.

14. The method of claim 1, wherein the dose that is subsequently administered to the subject is orally administered to the subject.

15. The method of claim 1, wherein the treatment is effective to achieve a target plasma concentration of about 300 ng/mL to about 750 ng/mL.

16. The method of claim 1, wherein the dose that is subsequently administered is about 25 mg twice daily of the CSA when the subject's plasma concentration is less than or about 750 ng/mL.

17. A method of treating a subject with heart failure (HF), comprising:
a. administering to the subject an initial dose of 25 mg twice daily of a cardiac sarcomere activator (CSA) for an initial time period,
b. subsequently administering to the subject a dose of the CSA based on the subject's plasma concentration of the CSA measured at about 2 weeks after the first administration of the initial dose,
wherein the dose of the CSA is (i) about 25 mg twice daily when the subject's plasma concentration of the CSA is greater than or about 300 ng/mL, or (ii) a dose greater than 25 mg twice daily when the subject's plasma concentration is less than 300 ng/mL; and
wherein the CSA is omecamtiv mecarbil, or a pharmaceutically acceptable salt thereof.

18. The method of claim 17, wherein the dose greater than 25 mg twice daily is 37.5 mg twice daily or 50 mg twice daily.

19. The method of claim 17, wherein the subject has chronic heart failure or a New York Heart Association Class II or III heart failure.

20. The method of claim 17, wherein the CSA is omecamtiv mecarbil dihydrochloride hydrate.

21. The method of claim 17, wherein the omecamtiv mecarbil, or a pharmaceutically acceptable salt thereof, is orally administered to the subject.

22. The method of claim 17, wherein the dose that is subsequently administered is about 25 mg twice daily.

23. The method of claim 17, wherein the dose that is subsequently administered is about 37.5 mg twice daily.

24. The method of claim 1, wherein the method further comprises administering to the subject a third dose of the CSA based on the subject's plasma concentration of the CSA measured at about 6 weeks after the first administration of the initial dose, wherein the third dose of the CSA is i) the same as the dose administered at step b), when the subject's plasma concentration of the CSA is less than about 750 ng/mL; ii) less than the dose administered at step b), when the subject's plasma concentration of the CSA is greater than or about 1000 ng/mL; or iii) the same as or less than the dose administered at step b), when the subject's plasma concentration of the CSA is greater than or about 750 ng/mL but less than 1000 ng/mL.

25. The method of claim 24, wherein the third dose is about 25 mg twice daily.

26. The method of claim 24, wherein the third dose is about 37.5 mg twice daily.

27. The method of claim 24, wherein the third dose is about 50 mg twice daily.

28. The method of claim 6 wherein the method further comprises administering to the subject a third dose of a CSA based on the subject's plasma concentration of the CSA measured at about 6 weeks after the first administration of the initial dose, wherein the third dose of the CSA is i) the same as the dose administered at step b), when the subject's plasma concentration of the CSA is less than about 750 ng/mL; ii) less than the dose administered at step b), when the subject's plasma concentration of the CSA is greater than or about 1000 ng/mL; or iii) the same as or less than the dose administered at step b), when the subject's plasma concentration of the CSA is greater than or about 750 ng/mL but less than 1000 ng/mL.

29. The method of claim 28, wherein the third dose is about 25 mg twice daily.

30. The method of claim 28, wherein the third dose is about 37.5 mg twice daily.

31. The method of claim 28, wherein the third dose is about 50 mg twice daily.

32. The method of claim 17, wherein the method further comprises administering to the subject a third dose of a CSA based on the subject's second plasma concentration of the CSA measured at about 4 weeks after the first administration of the initial dose.

33. The method of claim 32, wherein the third dose of the CSA is the same as the dose administered at step b), when the subject's second plasma concentration of the CSA is less than about 750 ng/mL.

34. The method of claim 32, wherein the third dose of the CSA is less than the dose administered at step b), when the subject's second plasma concentration of the CSA is greater than or about 1000 ng/mL.

35. The method of claim 32, the third dose of the CSA is the same as or less than the dose administered at step b), when the subject's second plasma concentration of the CSA is greater than or about 750 ng/mL but less than 1000 ng/mL.

36. The method of claim 32, wherein the third dose of the CSA is i) the same as the dose administered at step b), when the subject's second plasma concentration of the CSA is less than about 750 ng/mL; ii) less than the dose administered at step b), when the subject's second plasma concentration of the CSA is greater than or about 1000 ng/mL; or iii) the same as or less than the dose administered at step b), when the subject's second plasma concentration of the CSA is greater than or about 750 ng/mL but less than 1000 ng/mL.

37. The method of claim 32, wherein the third dose is about 25 mg twice daily.

38. The method of claim 32, wherein the third dose is about 37.5 mg twice daily.

39. The method of claim 32, wherein the third dose is about 50 mg twice daily.

* * * * *